(12) United States Patent
Brocchini et al.

(10) Patent No.: US 8,575,397 B2
(45) Date of Patent: Nov. 5, 2013

(54) DERIVATISATION OF BIOLOGICAL MOLECULES

(75) Inventors: Stephen James Brocchini, London (GB); Antony Robert Godwin, London (GB); Yiqing Tang, Farnham (GB); Andrew Lennard Lewis, Farnham (GB)

(73) Assignee: Biocompatibles UK Limited, Farnham (GB)

( * ) Notice: Subject to any disclaimer, the term of this patent is extended or adjusted under 35 U.S.C. 154(b) by 380 days.

(21) Appl. No.: 12/527,233

(22) PCT Filed: Feb. 12, 2008

(86) PCT No.: PCT/EP2008/051675
§ 371 (c)(1),
(2), (4) Date: Aug. 14, 2009

(87) PCT Pub. No.: WO2008/098930
PCT Pub. Date: Aug. 21, 2008

(65) Prior Publication Data
US 2010/0119484 A1 May 13, 2010

(30) Foreign Application Priority Data

Feb. 14, 2007 (EP) .................................... 07102418

(51) Int. Cl.
*C07C 319/00* (2006.01)
(52) U.S. Cl.
USPC .......................................................... 568/57
(58) Field of Classification Search
None
See application file for complete search history.

(56) References Cited

U.S. PATENT DOCUMENTS 5,840,712 A * 11/1998 Morgan et al. .................. 514/52

FOREIGN PATENT DOCUMENTS

| WO | 00/18807 A | 4/2000 |
| WO | 02/28929 A | 4/2002 |

(Continued)

OTHER PUBLICATIONS

Database Caplus Chemical Abstracts Service, Columbus, Ohio, US; Database Accession No. 2005:727401, Abstract of Ladmiral et al., Polymer Preprints (American Chemical Society, Division of Polymer Chemistry) (2005), 46(2), 366-367.*
Database Caplus Chemical Abstracts Service, Columbus, Ohio, US; Database Accession No. 1947:2167, Abstract of Brown et al., Journal of the Chemical Society (1946) 816-19.*

(Continued)

*Primary Examiner* — Karl J Puttlitz
(74) *Attorney, Agent, or Firm* — Sughrue Mion, PLLC

(57) ABSTRACT

The present disclosure relates to a new polymerization process in which ethylenically unsaturated monomers are polymerised by a living radical polymerization process in the presence of an initiator and a catalyst. Polymers produced by this new process are also thought to be novel and may be used to derivatise biological molecules to improve their efficacy as therapeutic treatments. A preferred polymer is of formula

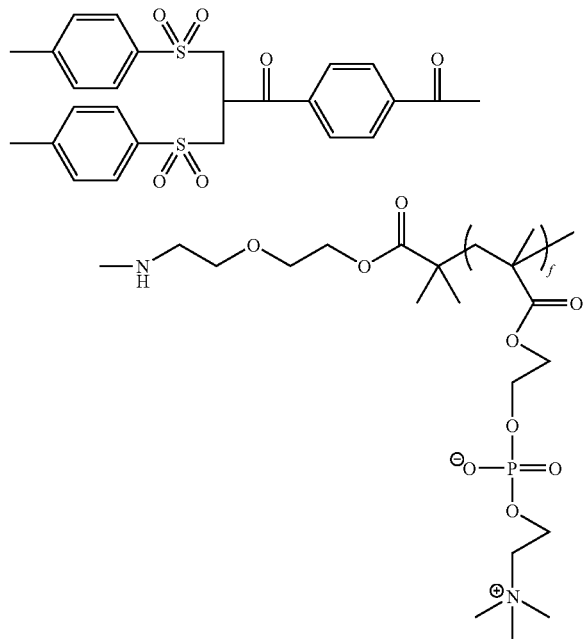

The polymers are particularly suitable for derivatising proteins, such as interferon-α.

5 Claims, 16 Drawing Sheets

(56) References Cited

FOREIGN PATENT DOCUMENTS

| WO | 03/062290 A | 7/2003 |
|---|---|---|
| WO | 2004/063237 A | 7/2004 |
| WO | 2004/113394 A | 12/2004 |
| WO | 2005/007197 A | 1/2005 |

OTHER PUBLICATIONS

Database Caplus Chemical Abstracts Service, Columbus, Ohio, US; Database Accession No. 1965:454348, Abstract of Wu et al., Yaoxue Xuebao (1965), 12(4), 254-66.*

Database Caplus Chemical Abstracts Service, Columbus, Ohio, US; Database Accession No. 1983:108428, Abstract of Kline, EP 64020.*

F.A. Liberatore et al., "Site-Directed Chemical Modification and Cross-Linking of a Monoclonal Antibody Using Equilibrium Transfer Alkylating Cross-Link Reagents", Bioconjugate Chemistry, vol. 1, No. 1, 1990, pp. 36-50 (XP002313939).

* cited by examiner

Key

1 SeeBlue Protein Markers
2 MPC-IFN with 30 kDa equivalent MPC
3 MPC-IFN with 20 kDa equivalent MPC
4 MPC-IFN with 12 kDa equivalent MPC
5 20 kDa PEG-IFN

DERIVATISATION OF BIOLOGICAL MOLECULES

The present invention relates to the modification of biological molecules for the purpose of improving their efficacy as therapeutic treatments.

Traditionally, therapeutic proteins have several inherent shortcomings. Proteins often have short half-lives, wide tissue distribution, the potential for immunogenicity, and sometimes need to be dosed frequently. When frequent dosing is required, it can result in increased cost, toxicity and complicated dosing regimens. In an effort to overcome these shortcomings, researchers have looked at improving the delivery systems of proteins. Among the potential solutions lies PEGylation, the attachment of a flexible strand or strands of polyethylene glycol (PEG) to a protein.

When attached to a drug or protein, PEG polymer chains can sustain bioavailability by protecting the drug molecules from immune responses and other clearance mechanisms. PEGylation has been shown to favourably alter pharmacokinetics by prolonging circulation time and decreasing clearance rates, to delay absorption, decrease systemic toxicity and to display increased clinical efficacy (partly by exhibiting reduced proteolysis).

Clinical developments are reported for PEG conjugates of proteins, peptides, aptamers, natural products and small molecules. For instance, PEG-asparaginase has been used in Oncaspar™ by Enzon to treat acute lymphoblastic leukemia and PEG-α-interferon 2b has been used by Schering Plough to treat Hepatitis C.

WO2005/007197 describes a series of novel reagents which can be used, inter alia, to conjugate thiol groups of two cysteine residues in a protein to give novel thioether conjugates. The reagents comprise polymers which may be, for example, a polyalkylene glycol, a polyacrylate or a HPMA polymer. It is disclosed that interferons may be conjugated, and their biological activity retained compared with non-conjugated interferons.

Overall, PEG attachment to interferon-alpha leads to a longer half-life of the interferon. This occurs due to decreased clearance by the kidney and reduced proteolysis (slower breakdown of protein). In addition, PEG attachment leads to lowered antigenicity of interferon. PEG attachment also leads to increased chemical and thermal (heat) stability of the base substance interferon.

PEGylation, however, has its disadvantages. PEGylation of proteins is known for its suboptimal yields; losses of 20-40% of protein and PEG-agent are not uncommon. Many of the common linking technologies are non-specific and the protein can be PEGylated at multiple sites in a random fashion, producing a mixture of products with variable activities. It is important, for optimised efficacy to ensure that the number of conjugated polymer molecules per protein is the same and that each polymer is attached to the same residue in each protein molecule.

Some have tried to avoid such problems by attaching PEG to the N-terminal amino group of proteins and peptides. This is called N-terminal PEGylation. N-terminal PEGylation may offer advantages in purification of the conjugates. It is also believed that the N-terminal PEGylation may better preserve bioactivity as compared to a random PEGylation of amino group of lysine residues.

Thiol specific polymer conjugating reagents for proteins have been developed. These are generally more hydrolytically stable than their amino-specific counterparts and thus can be used at lower stoichiometric excess. Conjugating functional moieties that are broadly selective for thiol groups include iodoacetamide, maleiimide (WO92/16221), vinyl-sulfone (WO95/13312 and WO95/34326), vinyl pyridines (WO88/05433), and acrylate and methacrylate esters (WO99/01469). These thiol selective conjugating moieties yield a single thioether conjugating bond between the polymer.

Conjugation to a protein via a thiol residue is also advantageous since proteins typically contain few thiol groups, hence conjugation can be specifically directed to a certain residue or residues on each protein.

This invention aims to address the issues with polymer-modification of therapeutic agents and provides a novel method for the attachment of a new class of polymers for biological molecule modification.

Herein we describe polymers of controlled architecture made using such methods known in the art as atom transfer radical polymerisation (ATRP) or radical addition-fragmentation chain transfer polymerisation (RAFT) (U.S. Pat. No. 6,852,816). Such methods have been described in WO02/28929 for producing zwitterionic polymers having controlled architectures, specifically having controlled chain length and/or blocked chain length in block polymers. Although these methods are well known, they have not previously been used for the preparation of compounds to conjugate biological molecules according to this invention.

We have previously described methods of attaching phospholipid-based polymers to proteins via conventional linking technologies described in the art (WO2004/063237) or by modification of the protein into an initiator for polymerisation of said polymers (WO03/062290). The present invention provides selective means for attaching polymers to biological molecules, combining the advantageous properties of polymers produced via living radical polymerisation with a reagent which is selective for particular groups on biological molecules, typically thiol groups.

The controlled molecular weight, composition and architectures of the various polymers brings about a high degree of control in the properties of the polymers.

In accordance with a first aspect of the present invention we provide a polymerisation process in which ethylenically unsaturated monomers are polymerised by a living radical polymerisation process in the presence of an initiator of the general formula I or II and a catalyst

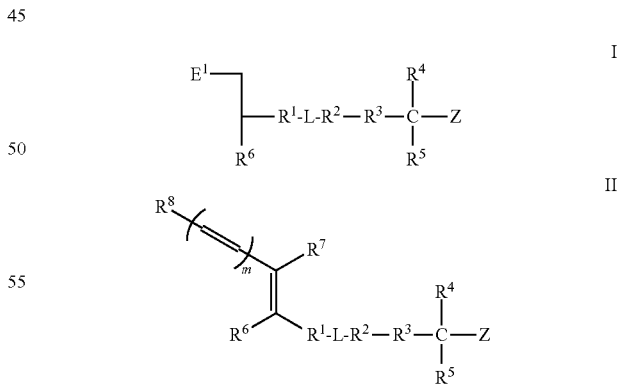

wherein $R^1$ is an electron-withdrawing group;

$R^2$ is selected from C=O, C(=O)$NR^9$ or a bond; wherein $R^9$ is H or $C_{1-4}$ alkyl;

$R^3$ is selected from the group consisting of $C_1$-$C_{20}$ alkylene, $C_3$-$C_8$ cycloalkylene, C(=O)$R^{10}$, C(=O)$NR^{11}$, $C_1$-$C_{20}$ alkoxy, $C_2$-$C_{20}$ alkenylene, $C_2$-$C_{20}$ alkenyl oxiranylene, arylene, heterocyclene and aralkylene; in which 0 to all of the hydrogen atoms are replaced with halogen, $C_1$-$C_6$ alkyl optionally substituted with 1 to 2 substituents selected from the group consisting of $C_1$-$C_4$ alkoxy, aryl, heterocyclyl, $C(=O)R^{13}$, $C(=O)NR^{11}R^{12}$, oxiranyl and glycidyl;

$R^{10}$ is alkylene of from 1 to 20 carbon atoms, alkoxy from 1 to 20 carbon atoms, oligo(alkoxy) in which each alkoxy group has from 1 to 3 carbon atoms, aryloxy or heterocycly-loxy; any of which groups may have substituents selected from optionally substituted alkoxy, oligoalkoxy, amino (including mono- and di-alkyl amino and trialkyl ammonium, which alkyl groups, in turn, may have substituents selected from acyl, alkoxycarbonyl, alkenoxycarbonyl, aryl and hydroxy) and hydroxyl groups;

$R^{11}$ and $R^{12}$ are independently H or alkyl of from 1 to 20 carbon atoms, or $R^{11}$ and $R^{12}$ may be joined together to form an alkanediyl group of from 2 to 5 carbon atoms, thus forming a 3- to 6-membered ring;

$R^4$ and $R^5$ are each independently selected from H, Z, halogen, $C_{1-20}$ alkyl, $C_3$-$C_8$ cycloalkyl, OH, CN, $C_2$-$C_{20}$ alkenyl, $C_2$-$C_{20}$ alkenyl oxiranyl, $C(=O)R^{13}$, glycidyl, aryl, heterocyclyl, arylkyl, aralkenyl, in which 0 to all of the hydrogen atoms are replaced with halogen, $C_1$-$C_6$ alkyl optionally substituted with 1 to 2 substituents selected from the group consisting of $C_1$-$C_4$ alkoxy, aryl, heterocyclyl, $C(=O)R^{13}$, $C(=O)NR^{11}R^{12}$, oxiranyl and glycidyl;

where $R^{13}$ is alkyl of from 1 to 20 carbon atoms, alkoxy of from 1 to 20 carbon atoms, oligo(alkoxy) in which each alkoxy group has 1 to 3 carbon atoms, aryloxy or heterocyclyloxy any of which groups may have substituents selected from optionally substituted alkoxy, oligoalkoxy, amino (including mono- and di-alkyl amino and trialkyl ammonium, which alkyl groups, in turn may have substituents selected from acyl, alkoxycarbonyl, alkenoxycarbonyl, aryl and hydroxy) and hydroxyl groups; and L is a linking group;

Z is selected from the group consisting of Cl, Br, I, $OR^{14}$, $SR^{15}$, $SeR^{15}$, $OP(=O)R^{15}$, $OP(=O)(=OR^{15})_2$, $O-N(R^{15})_2$ and $S-C(=S)N(R^{15})_2$, where $R^{14}$ is alkyl of from 1 to 20 carbon atoms in which each of the hydrogen atoms may be independently replaced by halide, $R^{15}$ is aryl or a straight or branched $C_1$-$C_{20}$ alkyl group, and where an $N(R^{15})_2$ group is present, the two $R^{15}$ groups may be joined to form a 5- or 6-membered heterocyclic ring;

$R^6$ is $CH_2E^2$, H or $C_{1-4}$ alkyl;

$R^7$ and $R^8$ are each independently selected from H and $C_{1-4}$ alkyl;

m is 0-4; and $E^1$ and $E^2$ are each, independently, a leaving group, or a precursor to a leaving group.

Compounds of general formula I or II are also novel. Accordingly, a second aspect of this invention provides compounds of general formula I or II

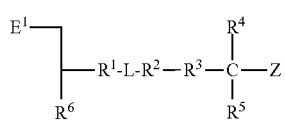

I

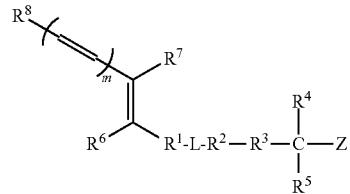

II wherein $R^1$-$R^5$, $R^7$-$R^8$ (if present), L, Z, m and $E^1$ are as defined above in the first aspect of this invention.

According to a third aspect of the present invention, we provide a polymer of general formula VII or VIII

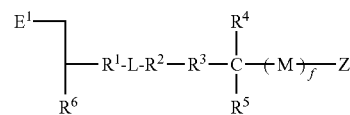

VII

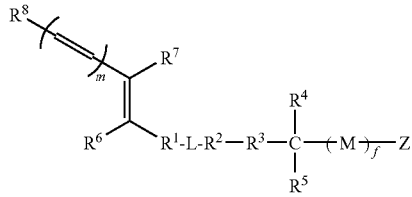

VIII wherein $R^1$-$R^6$, $R^7$-$R^8$ (if present), L, Z, m and $E^1$ are as defined in the first aspect of the invention f is 1 to 500; and Groups M are the same or different and are residues of ethylenically unsaturated monomers.

These novel polymers are preferably produced in a process according to the first aspect of this invention.

The novel polymers may be used to derivatise biological molecules. Accordingly, the fourth aspect of this invention provides a method of derivatisation of a biological molecule in which a polymer of general formula X or general formula XI

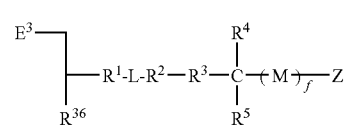

X

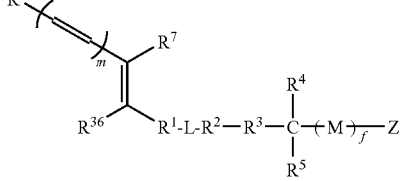

XI is added to a biological molecule of general formula $T^1D^1X$ or to biological molecules of general formula $T^1D^1X$ and $T^2D^2X$, wherein D is S, NH or O and X is H, $D^1T^1$ or $D^2T^2$ to form an adduct of general formula XII or of general formula XIII

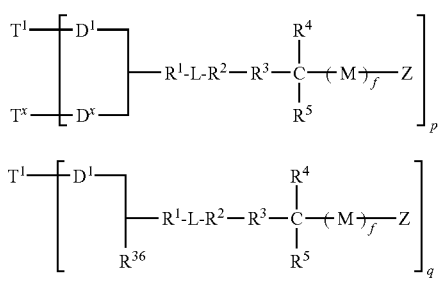

wherein $R^1$-$R^5$, $R^7$-$R^8$ (if present), m and L are as defined in the first aspect of the invention and M is as defined above in the third aspect of the invention;

f is 1 to 500;

$R^{36}$ is —$CH_2E^4$, H or $C_{1-4}$ alkyl; and $E^3$ and $E^4$ are each, independently, a leaving group, x is 1 or 2;

p is 1-5 and q is 1-10.

We provide in a fifth aspect of this invention novel compounds of general formula XII or XIII as defined above.

The sixth aspect of this invention provides a pharmaceutical composition comprising a novel compound of general formula XII or XIII and a pharmaceutically acceptable carrier.

A final aspect of this invention is the novel compound of general formula XII or XIII, for use in therapy.

Compounds of general formula I and II act as initiators in the living radical polymerisation process according to the first aspect of the present invention. The initiators are extended at the carbon to which Z is attached by a living radical polymerisation process. The opposite end of the initiator molecule must be suitable for derivatisation with a biological molecule. In this regard it is vital that the initiator has an α-methylene leaving group, or precursor to a leaving group, or a double bond conjugated with an electron-withdrawing group. This allows a biological molecule to react with the initiator in a Michael reaction.

When referring to groups which are radicals, it is intended that the group can be joined to adjacent groups in either direction. For instance when $R^3$ is C(=O)$R^{10}$, it may be linked either $R^2$—C(=O)$R^{10}$—C in the compounds of general formula (I), (II), (VII), (VIII), (XI), (XII) and (XIII), or $R^2$-$R^{10}$C(=O)—C.

Preferably, in compounds of formula I and II, $R^6$ is —$CH_2E^2$. If the leaving group is prone to elimination rather than to direct displacement with a nucleophile, and the electron-withdrawing group $R^1$ is a suitable activating moiety for the Michael reaction then sequential intramolecular bis-alkylation can occur by consecutive Michael and retro Michael reactions. The leaving moiety serves to mask a latent conjugated double bond that is not exposed until after the first alkylation has occurred and bis-alkylation results from sequential Michael and retro-Michael reactions.

Initiators of general formula II may have from 1 to 5 double bonds. A nucleophile may add to the conjugated system at a suitable position on any of the double bonds. Preferably, however, m is zero in an initiator of general formula II.

Preferably, in the initiators of general formula I and II, $R^6$, $R^7$ and $R^8$ are each independently selected from —H or —$CH_3$.

In the initiator of general formula I or II it is preferred that only one of W and $R^5$ is H. Preferably, neither are hydrogen. Suitably, at least one, and preferably both of $R^4$ and $R^5$ are methyl.

In a preferred embodiment, $R^3$ is —CO—$R^{10}$ in which $R^{10}$ is oligoalkoxy, preferably oligoethoxy in which there are 2 to 10 ethoxy groups. Alternatively, the alkoxy group may have 1 or 3 carbon atoms. In this preferred embodiment, $R^4$ and $R^5$ are preferably methyl.

Group Z is a radically transferable group and is preferably a halogen, more preferably Cl, Br or I, most preferably Br. Since groups $R^4$ and $R^5$ may also be Z the initiator may be di-, oligo- or poly-functional.

Suitable linking groups, L, include a bond, a $C_{1-10}$ alkylene group, or an optionally substituted aryl or heteroaryl, any of which groups may have substituents selected from optionally substituted alkoxy, oligoalkoxy, amino (including mono- and di-alkyl amino and trialkyl ammonium, which alkyl groups, in turn, may have substituents selected from acyl, alkoxycarbonyl, alkenoxycarbonyl, aryl and hydroxy) and hydroxyl groups.

Suitable groups for electron-withdrawing group $R^1$ include a keto group, an ester group, and a sulphone group.

Groups $E^1$ and $E^2$ are typically leaving groups selected from —$SR^{17}$, —$SO_2R^{17}$, —$OSO_2R^{17}$, —$N^+R^{17}_3$, —$N^+HR_2^{17}$, —$N^+H_2R^{17}$, halogen, or —OAr, in which $R^{17}$ represents an alkyl or aryl group and Ar represents a substituted aryl group containing at least one electron-withdrawing substituent.

Alternatively, groups $E^1$ and $E^2$ may be precursors to leaving groups, wherein the leaving group may be obtained by a simple chemical reaction such as oxidation or reduction. Having $E^1$ and $E^2$ as precursors to leaving groups may be preferable if this facilitates synthesis of the initiator and the subsequent polymerisation reaction.

In a preferred embodiment of this invention, $E^1$ and $E^2$ are each, independently, an (optionally substituted) aryl sulfide or aryl sulfone group.

An aryl sulfide (a precursor to a leaving group) may be converted into an aryl sulfone (a leaving group) by a simple oxidation reaction, as is well know in the art. The process according to the first aspect of this invention may include a subsequent reaction step in which groups $E^1$ and $E^2$ (if present) which are precursors to leaving groups are converted into leaving groups.

A particularly preferred initiator of general formula I has formula

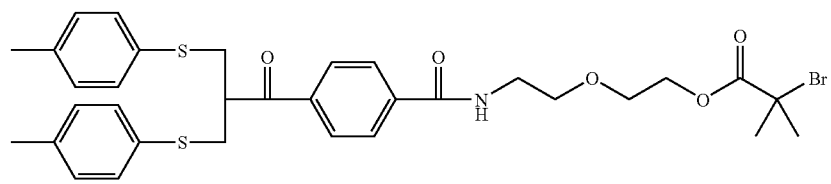

The living radical polymerisation process of the invention may be a group transfer radical polymerisation, for instance in which an N—O, or other carbon-, sulphur-, and oxygen-centered radical group is transferred from an initiator compound to a monomer. Preferably, however, the process is an atom transfer radical polymerisation process.

The novel polymers according to the third aspect of this invention are preferably made by the living radical polymerisation process of the first aspect of the invention. Other controlled polymerisation techniques may be used for instance NO group transfer systems such as are described in WO-A-0018807, catalyst systems described in WO-A-9958588, systems involving irradiation with visible light, or other EM radiation such as described in WO-A-99/10387, radical addition fragmentation chain transfer polymerisation (RAFT) as described in Rizzardo, E. et al. ACS Symposium Series 2000, 768, 278-296, using compounds (initiators) of the general type Z—C=SSR or macromolecular design through interchange of xanthes (MADIX) as descried by Bontevin, B., J. Polym. Sci. PtA, Polym. Chem., 2000, 38(18), 3235-3243.

Atom or group transfer radical polymerisation processes are described further in WO 02/28929.

Selection of a suitable ligand is, for instance, based upon the solubility characteristics and/or the separability of the catalyst from the product polymer mixture. Generally it is catalyst to be soluble in a liquid reaction mixture, although under some circumstances it may be possible to immobilise the catalyst, for instance an a porous substrate. For the preferred process, which is carried out in the liquid phase, the ligand is soluble in a liquid phase. The ligand is generally a nitrogen containing ligand. The preferred ligand may be a compound including a pyridyl group and an amino moiety, such as bipyridine, or

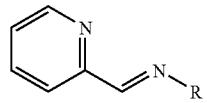

where R is a suitable alkyl group, the substituent being variable and adaptable to confer desired solubility characteristics or may be triphenylphosphine or 1,1,4,7,10,10-hexamethyltriethylene tetramine.

Such ligands are usefully used in combination with copper chloride and ruthenium chloride transition metal compounds as part of the catalyst.

The living radical polymerisation process of the invention is preferably carried out to achieve a degree of polymerisation in the range 5 to 500. Preferably the degree of polymerisation is in the range 10 to 100, more preferably in the range 10 to 50. In the preferred group or atom transfer radical polymerisation technique, the degree of polymerisation is directly related to the initial ratios of initiator to monomer. Preferably the ratio is in the range 1:(5 to 500), more preferably in the range of 1:(10 to 100), most preferably in the range 1:(10 to 50).

The ratio of metal compound and ligand in the catalyst should be approximately stoichiometric, based on the ratios of the components when the metal ion is fully complexed. The ratio should preferably be in the range 1:(0.5 to 2) more preferably in the range 1:(0.8:1.25). Preferably the range is about 1:1.

In the process, the catalyst may be used in amounts such that a molar equivalent quantity as compared to the level of initiator is present. However, since catalyst is not consumed in the reaction, it is generally not essential to include levels of catalyst as high as of initiator. The ratio of catalyst (based on transition metal compound) to initiator is preferably in the range 1:(1 to 50), more preferably in the range 1:(1 to 10).

Whilst the polymerisation reaction may be carried out in the gaseous phase, it is more preferably carried out in the liquid phase. The reaction may be heterogeneous, that is comprising a solid and a liquid phase, but is more preferably homogeneous. Preferably the polymerisation is carried out in a single liquid phase. Where the monomer is liquid, it is sometimes unnecessary to include a non-polymerisable solvent. More often, however, the polymerisation takes place in the presence of a non-polymerisable solvent. The solvent should be selected having regard to the nature of the zwitterionic monomer and any comonomer, for instance for its suitability for providing a common solution containing both monomers. The solvent may comprise a single compound or a mixture of compounds.

The ethylenically unsaturated comonomers polymerised in the process according to the first aspect of this invention may be anionic, cationic or nonionic monomers. Two or more different ethylenically unsaturated comonomers may be polymerised.

The ethylenically unsaturated comonomers preferably have general formula III

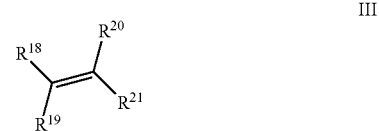

in which $R^{18}$ is selected from hydrogen, halogen, $C_{1-4}$ alkyl and groups $COOR^{22}$ in which $R^{22}$ is hydrogen and $C_{1-4}$ alkyl;

$R^{19}$ is selected from hydrogen, halogen and $C_{1-4}$ alkyl;

$R^{20}$ is selected from hydrogen, halogen, $C_{1-4}$ alkyl and groups $COOR^{22}$ provided that $R^{18}$ and $R^{20}$ are not both $COOR^{22}$; and $R^{21}$ is a $C_{1-10}$ alkyl, a $C_{1-20}$ alkoxycarbonyl, a mono- or di-($C_{1-20}$ alkyl)amino carbonyl, a $C_{6-20}$ aryl (including alkaryl), a $C_{7-20}$ aralkyl, a $C_{6-20}$ aryloxycarbonyl, a $C_{1-20}$-aralkyloxycarbonyl, a $C_{6-20}$ arylamino carbonyl, a $C_{7-20}$ aralkyl-amino, a hydroxyl or a $C_{2-10}$ acyloxy group, any of which may have one or more substituents selected from halogen atoms, alkoxy, oligo-alkoxy, aryloxy, acyloxy, acylamino, amine (including mono and di-alkyl amino and tri-alkylammonium), carboxyl, sulphonyl, phosphoryl, phosphino, (including mono- and di-alkyl phosphine and tri-alkylphosphonium), zwitterionic and hydroxyl groups;

or $R^{21}$ and $R^{20}$ or $R^{21}$ and $R^{19}$ may together form —$CONR^{23}CO$ in which $R^{23}$ is a $C_{1-20}$ alkyl group.

In a preferred embodiment, $R^{18}$ and $R^{19}$ are each hydrogen, $R^{20}$ is methyl and $R^{21}$ is a $C_{1-20}$ alkoxy carbonyl, optionally having a hydroxy substituent.

In the polymers of general formula VII and VIII, residues M correspond to the ethylenically unsaturated monomers used in the process according to the first aspect of the invention. Preferably residues M are selected from radicals of the general formula IX.

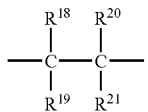

IX in which $R^{18}$ is selected from hydrogen, halogen, $C_{1-4}$ alkyl and groups $COOR^{22}$ in which $R^{22}$ is hydrogen and $C_{1-4}$ alkyl;

$R^{19}$ is selected from hydrogen, halogen and $C_{1-4}$ alkyl;

$R^{20}$ is selected from hydrogen, halogen, $C_{1-4}$ alkyl and groups $COOR^{22}$ provided that $R^{18}$ and $R^{20}$ are not both $COOR^{22}$; and $R^{21}$ is a $C_{1-10}$ alkyl, a $C_{1-20}$ alkoxycarbonyl, a mono- or di-($C_{1-20}$ alkyl)amino carbonyl, a $C_{6-20}$ aryl (including alkaryl), a $C_{7-20}$ aralkyl, a $C_{6-20}$ aryloxycarbonyl, a $C_{1-20}$-aralkyloxycarbonyl, a $C_{6-20}$ arylamino carbonyl, a $C_{7-20}$ aralkyl-amino, a hydroxyl or a $C_{2-10}$ acyloxy group, any of which may have one or more substituents selected from halogen atoms, alkoxy, oligo-alkoxy, aryloxy, acyloxy, acylamino, amine (including mono and di-alkyl amino and trialkylammonium), carboxyl, sulphonyl, phosphoryl, phosphino, (including mono- and di-alkyl phosphine and trialkylphosphonium), zwitterionic and hydroxyl groups;

or $R^{21}$ and $R^{20}$ or $R^{21}$ and $R^{19}$ may together form —$CONR^{23}CO$ in which $R^{23}$ is a $C_{1-20}$ alkyl group.

Typically, in these polymers, f is in the range 5 to 50.

The ethylenically unsaturated monomers may polymerise to form a polymer selected from polyalkylene glycol, polyvinylpyrrolidone, polyacrylate, polyoxazoline, polyvinylalcohol, polyacrylamide, polymetharylamide, or a HPMA copolymer. Alternatively, the polymer may be susceptible to enzymatic or hydrolytic degradation, such as polyesters, polyacetals, poly(ortho esters), polycarbonates and polyamides.

The polymer may be a homopolymer that is moiety -(-M-)-$_f$ in polymers of general formula VII and VIII may comprise groups M which are residues of the same ethylenically unsaturated monomer. Alternatively, the polymer may be a copolymer or a block copolymer, wherein groups M in moiety -(-M-)-$_f$ are residues of different ethylenically unsaturated monomers.

Preferably, the ethylenically unsaturated comonomers are zwitterionic. The zwitterionic nature arises from the combination of a cationic and anionic moiety. The cationic moiety may be an ammonium, phosphonium or sulphonium group, preferably an ammonium group. The anion is typically a phospho moiety, more typically a phosphate diester.

$R^{21}$ is preferably a group of general formula IV

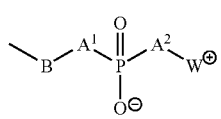

IV in which the moieties $A^1$ and $A^2$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group, preferably in which $W^+$ is a group of formula

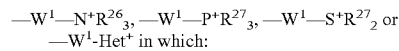

in which:

$W^1$ is alkanediyl of 1 or more, preferably 2-6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups;

B is a bond, or a straight or branched chain alkanediyl, alkylene oxaalkylene, or alkylene (oligooxalkylene) group, optionally containing one or more fluorine substituents; and either the groups $R^{26}$ are the same or different and each is hydrogen or alkyl of 1 to 4 carbon atoms, preferably methyl, or aryl, such as phenyl, or two of the groups $R^{26}$ together with the nitrogen atom to which they are attached form an aliphatic heterocyclic ring containing from 5 to 7 atoms, or the three groups $R^{26}$ together with the nitrogen atom to which they are attached form a fused ring structure containing from 5 to 7 atoms in each ring, and optionally one or more of the groups $R^{26}$ is substituted by a hydrophilic functional group, and the groups $R^{27}$ are the same or different and each is $R^{26}$ or a group $OR^{26}$, where $R^{26}$ is as defined above; or Het is an aromatic nitrogen-, phosphorus- or sulphur-, preferably nitrogen-, containing ring, for example pyridine.

More preferably, $R^{21}$ is of general formula

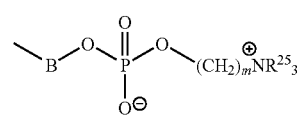

V where the groups $R^{25}$ are the same or different and each is hydrogen or $C_{1-4}$ alkyl, and m is from 1 to 4, in which preferably the groups $R^{27}$ are the same preferably methyl.

Alternatively, $R^{21}$ may be of the general formula VI.

In formulae IV-VI, B is preferably a straight chain $C_{2-6}$ alkanediyl.

An example of a suitable zwitterionic monomer is 2-methacryloyloxyethyl-phosphorylcholine (MPC).

The living radical polymerisation process of the invention is preferably carried out to achieve a degree of polymerisation in the range 5 to 500. Preferably the degree of polymerisation is in the range 10 to 100, more preferably in the range 10 to 50. In the preferred group or atom transfer radical polymerisation technique, the degree of polymerisation is directly related to the initial ratios of initiator to monomer. Preferably the ratio is in the range 1:(5 to 500), more preferably in the range of 1:(10 to 100), most preferably in the range 1:(10 to 50).

The ratio of metal compound and ligand in the catalyst should be approximately stoichiometric, based on the ratios of the components when the metal ion is fully complexed. The ratio should preferably be in the range 1:(0.5 to 2) more preferably in the range 1:(0.8:1.25). Preferably the range is about 1:1.

In the process, the catalyst may be used in amounts such that a molar equivalent quantity as compared to the level of initiator is present. However, since catalyst is not consumed in the reaction, it is generally not essential to include levels of catalyst as high as of initiator. The ratio of catalyst (based on transition metal compound) to initiator is preferably in the range 1:(1 to 50), more preferably in the range 1:(1 to 10).

Whilst the polymerisation reaction may be carried out in the gaseous phase, it is more preferably carried out in the liquid phase. The reaction may be heterogeneous, that is comprising a solid and a liquid phase, but is more preferably homogeneous. Preferably the polymerisation is carried out in a single liquid phase. Where the monomer is liquid, it is sometimes unnecessary to include a non-polymerisable solvent. More often, however, the polymerisation takes place in the presence of a non-polymerisable solvent. The solvent should be selected having regard to the nature of the zwitterionic monomer and any comonomer, for instance for its suitability for providing a common solution containing both monomers. The solvent may comprise a single compound or a mixture of compounds.

It has been found that, especially where the zwitterionic monomer is MPC, that it is desirable to include water in the polymerisation mixture. Preferably water should be present in an amount in the range 10 to 100% by weight based on the weight of ethylenically unsaturated monomer. Preferably the total non-polymerisable solvent comprised 1 to 500% by weight based on the weight of ethylenically unsaturated monomer. It has been found that the zwitterionic monomer and water should be in contact with each other for as short a period as possible prior to contact with the initiator and catalyst. It may be desirable therefore for all the components of the polymerisation other than the zwitterionic monomer to be premixed and for the zwitterionic monomer to be added to the premix as the last additive.

It is often desired to copolymerise MPC or other zwitterionic monomer with a comonomer which is insoluble in water. In such circumstances, a solvent or co-solvent (in conjunction with water) is included to confer solubility on both MPC and the more hydrophobic monomer. Suitable organic solvents are ethers, esters and, most preferably, alcohols. Especially where a mixture of organic solvent and water is to used, suitable alcohols are $C_{1-4}$-alkanols. Methanol is found to be particularly suitable in the polymerisation process of the invention.

The process may be carried out at raised temperature, for instance up to 60 to 80° C. However it has been found that the process proceeds sufficiently fast at ambient temperature.

The polymerisation process of the invention has been found to provide polymers of zwitterionic monomers having a polydispersity (of molecular weight) of less than 1.5, as judged by gel permeation chromatography. Polydispersities in the range 1.2 to 1.4 have been achieved. Conversion rates achieved in the process are over 90% often over 95% or higher. It is preferred that the process be continued until a conversion level of at least 50%, or usually, at least 70% is reached.

It is believed that this process is the first time that low polydispersity polymers have been formed of monomers of the general formula III using an initiator of general formula I or II and such polymers form a further aspect of the invention.

In polymers of general formula VII and VIII, the preferred groups L, $R^1$-$R^6$, Z and m are the same as for the initiator of general formula I or II. Similarly, the preferred groups for $E^1$ and $E^2$ are as for the initiator compounds. However, for the novel compounds to be able to conjugate biological molecules, groups $E^1$ and $E^2$ (if present) should be leaving groups. Accordingly, a particularly preferred leaving group is:

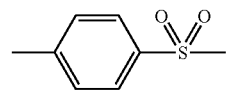

and particularly preferred polymers are of formula:

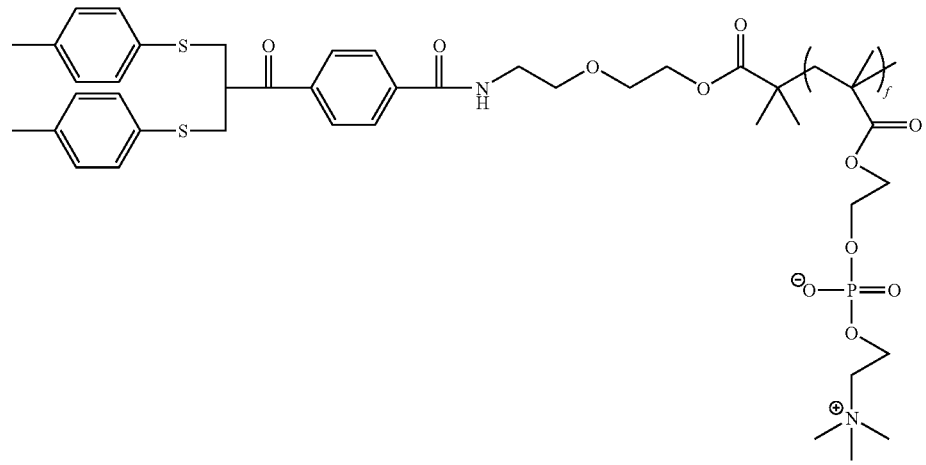

and

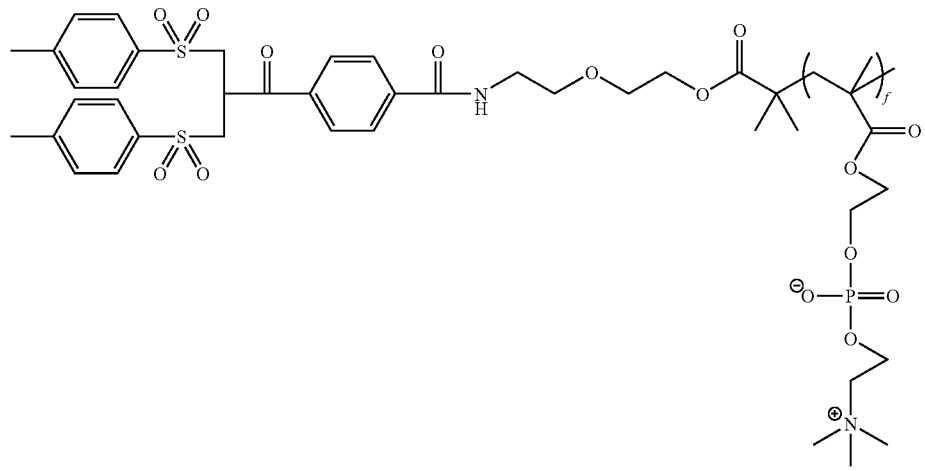

The method according to the fourth aspect of this invention provides a novel method of derivatisation of a biological molecule(s). The biological molecule or molecules are represented by general formula $T^1D^1X$ and $T^2D^2X$ wherein $D^1X$ and $D^2X$ represent a nucleophillic group. Typically, the nucleophillic group is a thiol group, although amine and hydroxyl groups may also have utility.

An adduct of general formula XIII is formed when the polymer of general formula X or XI has only one leaving group, or $R^{36}$ is not a leaving group in a polymer of general formula XI. Adducts of general formula XII may form when a nucleophile attacks the polymer of general formula X or XI twice, i.e. when there are two leaving groups ($E^3$ and $E^4$), or $R^{36}$ is a leaving group in XI.

Moiety $T^x$-$D^x$- in formula XII may be derived from the same biological molecule as $T^1$-$D^1$, in which case x is 1. Alternatively, moiety $T^x$-$D^x$- may be derived from a different biological molecule, in which case x is 2.

Typically, the derivatisation will be carried out by partially reducing a disulphide bond derived from two cysteine amino acids in the same protein. Since in this case $T^1D^1$ and $T^xD^x$ are derived from the same protein, x=1.

Suitably, the process according to the invention is carried out by partially reducing a disulfide bond derived from two cysteine amino acids in the protein in situ following which the reduced product reacts with the polymer of formula X or XI. Disulfides can be reduced, for example, with dithiothreitiol, mercaptoethanol, or tris-carboxyethylphosphone using conventional methods. The process may be carried out in a solvent or solvent mixture in which all reactants are soluble. The biological molecule containing nucleophilic groups (e.g. protein) may be allowed to react directly with the polymer of the general formula X or XI in an aqueous reaction medium. This reaction medium may also be buffered, depending on the pH requirements of the nucleophile. The optimum pH for the reaction is generally between about 5.5 and about 8, for example 7.4, preferably about 6.0-6.5. Reaction temperatures between 3-37° C. are generally suitable: proteins and other biological molecules may decompose or denature impairing function if the conjugation reaction is conducted at a temperature where these processes may occur. Reactions conducted in organic media (for example THF, ethyl acetate, acetone) are typically conducted at temperatures up to ambient, for example temperatures below 0° C.

A protein can contain one or a multiplicity of disulfide bridges. Reduction to give free sulfhydral moieties can be conducted to reduce one or a multiplicity of disulfide bridges in a protein. Depending on the extent of disulfide reduction in the stoichiometry of the polymeric conjugation reagent that is used, it is possible to conjugate one or a multiplicity of polymer molecules to the protein. Immobilised reducing agents may be used if it is desired to reduce less than the total number of disulfides, as can partial reduction using different reaction conditions or the addition of denatures.

Alternatively the source of the thiol groups can be from cysteines or thiols not originally derived from a disulfide bridge. If the source of the thiol groups is a disulfide bridge, this may be intrachain or interchain.

The biological molecule can be effectively conjugated with the polymers of the present invention using a stoichiometric equivalent or a slight excess of polymer, unlike many prior art reagents. However, since the polymers of the present invention do not undergo competitive reactions with aqueous media used to solvate proteins, it is possible to conduct conjugation reaction with an excess stoichiometry of polymer. The excess polymer can be easily removed by ion exchange chromatography during routine purification of proteins.

The biological molecule is preferably a peptide, protein or lipoprotein. The protein may be, for example, a polypeptide, antibody, antibody fragment, enzyme, cytokine, chemokine or receptor. Constrained or cyclic polypeptides, which are usually cyclised through a disulphide bridge, and epitopes, may also be used.

The following gives some specific biological molecules which may have utility in the present invention, depending upon the desired application. Enzymes include carbohydrate-specific enzymes, proteolytic enzymes and the like. Enzymes of interest, for both industrial (organic based reactions) and biological applications in general and therapeutic applications in particular include the oxidoreductases, transferases, hydrolases, lyases, isomerases and ligases disclosed by U.S. Pat. No. 4,179,337. Specific enzymes of interest include asparaginase, arginase, adenosine deaminase, superoxide dismutase, catalase, chymotrypsin, lipase, uricase, bilirubin oxidase, glucose oxidase, glucuronidase, galactosidase, glucocerbrosidase, and glutaminase.

The biological molecules conjugated in the present invention include for example factor 8, insulin, ACTH, glucagen, somatostatin, somatotropins, thymosin, parathyroid hormone, pigmentary hormones, somatomedins, erythropoietin, luteinizing hormone, hypothalamic releasing factors, antidiuretic hormones, prolactin, interleukins, interferons, colony stimulating factors, hemoglobin, cytokines, antibodies, glycopolypeptides such as immunoglobulins, ovalbumin, lipase, glucocerebrosidase, lectins, tissue plasminogen activator and glycosilated inerleukins, interferons and colony stimulating factors are of interest, as are immunoglobulins such as IgG, IgE, IgM, IgA, IgD and fragments thereof. The biological molecule is preferably a peptide hormone.

Of particular interest are antibodies and antibody fragments which are used in clinical medicine for diagnostic and therapeutic purposes. The antibody may be used alone or may be used covalently conjugated ("loaded") with another atom or molecule such as a radioisotope or a cytotoxic/antiinfective drug. Epitopes may be used for vaccination to produce an immunogenic polymer-protein conjugate.

Preferably, the protein is interferon-α.

The invention will now be illustrated by the following Examples, which refer to FIGS. 1-14, in which FIG. 1 shows the mechanism of PC-polymer insertion into a protein disulfide bridge;

Figure 12:
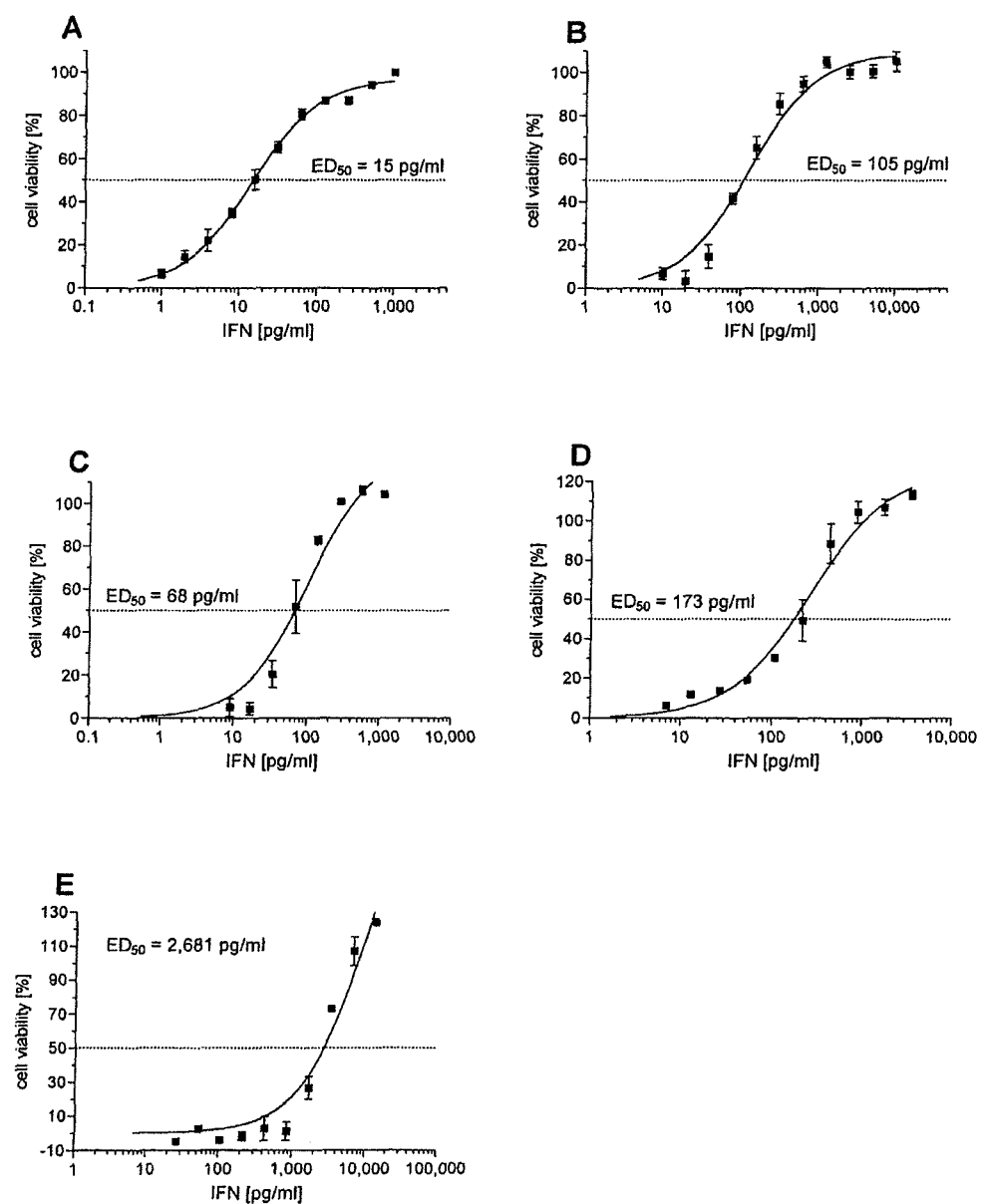
Figure 13:
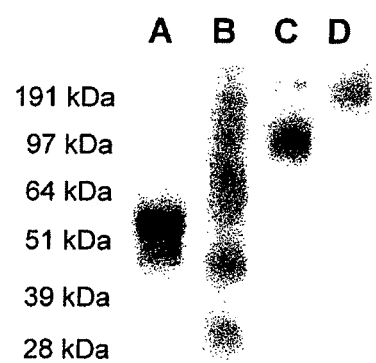
Figure 14:
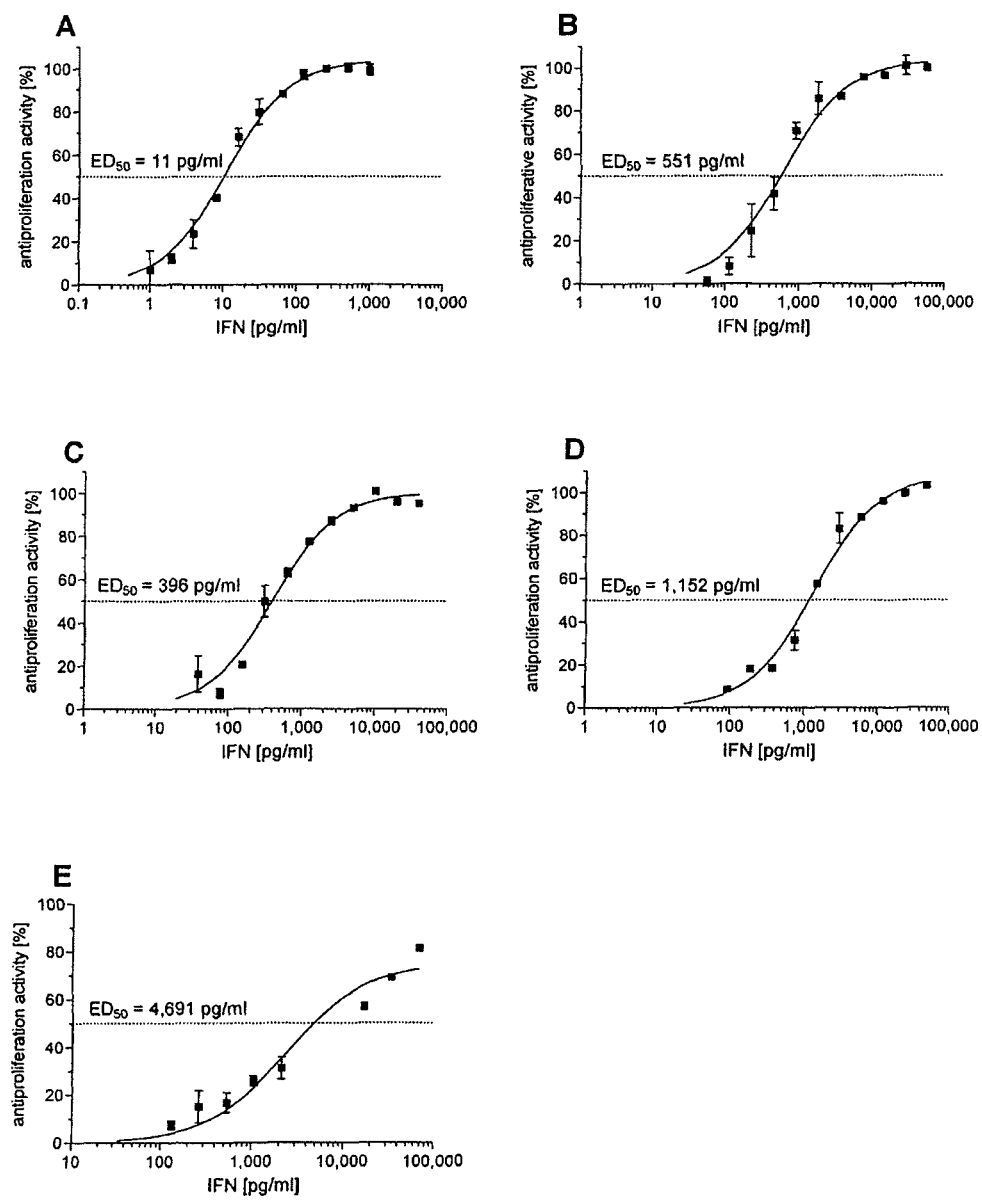
Figure 15:
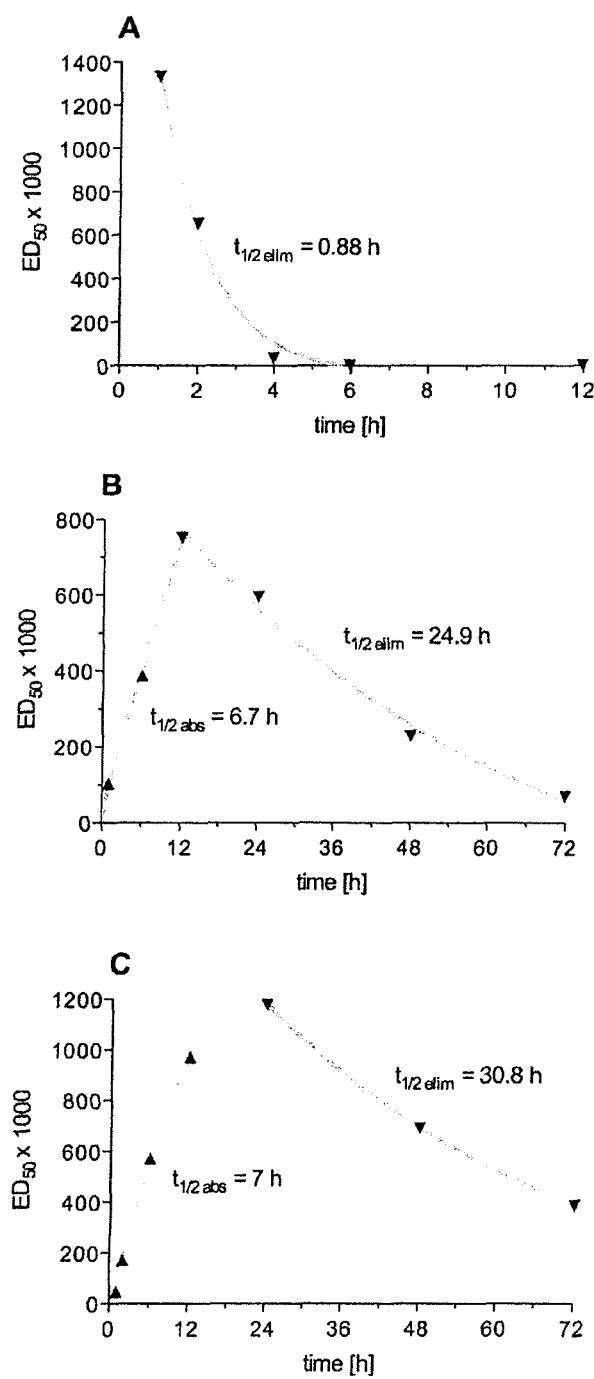
Figure 16:
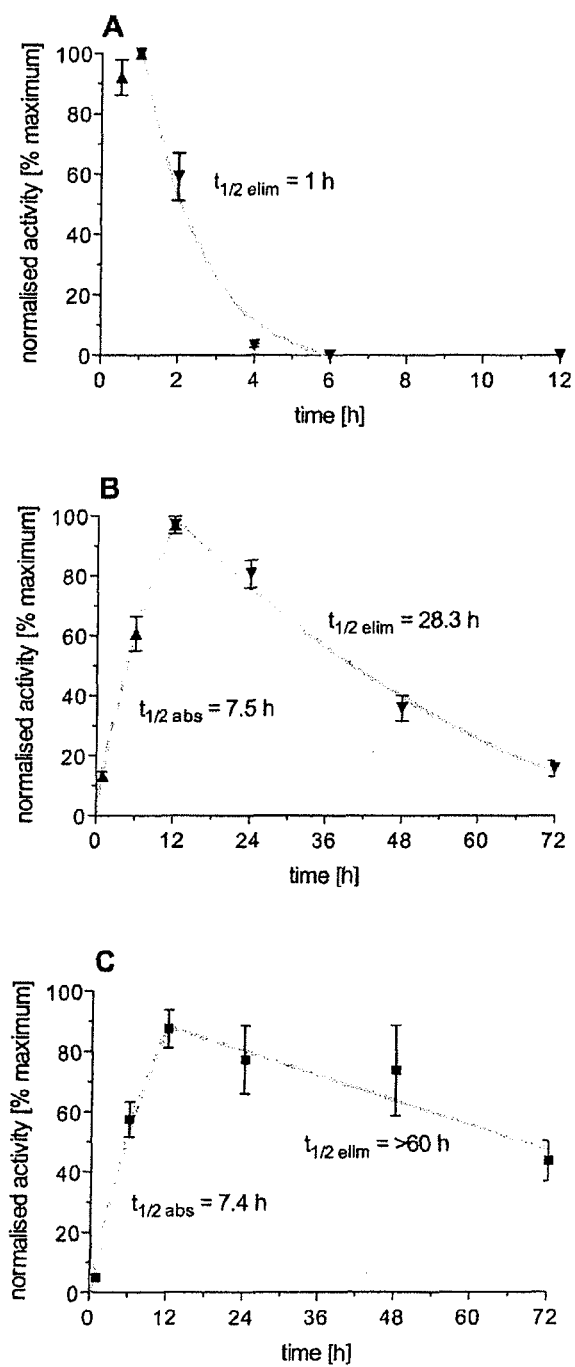

FIG. 12 displays representative graphs showing the antiviral activity of (A) IFN, (B) Con9(4), (C) Con9(2), (D) Con9(3), and (E) Con9(1);

FIG. 13 shows a Western blot with anti-IFN antibody from PAGE analysis showing (A) Con9(4), (B) Con9(1), (C) Con9(2), and (D) Con9(3);

FIG. 14 displays representative graphs showing the antiproliferation activity of (A) IFN, (B) Con9(4), (C) Con9(2), (D) Con9(3), and (E) Con9(1);

FIG. 15 shows representative pharmacokinetic profiles of (A) IFN-α2a (Roferon-A), (B) 20 kDa PEG equivalent MPC-IFN and (C) 40 kDa PEG-IFN (Pegasys) in mice; and FIG. 16 shows combined pharmacokinetic profiles of (A) IFN-α2a (Roferon-A), (B) 20 kDa PEG equivalent MPC-IFN and (C) 40 kDa PEG-IFN (Pegasys) in mice.

REFERENCE EXAMPLE 1

Figure 1:
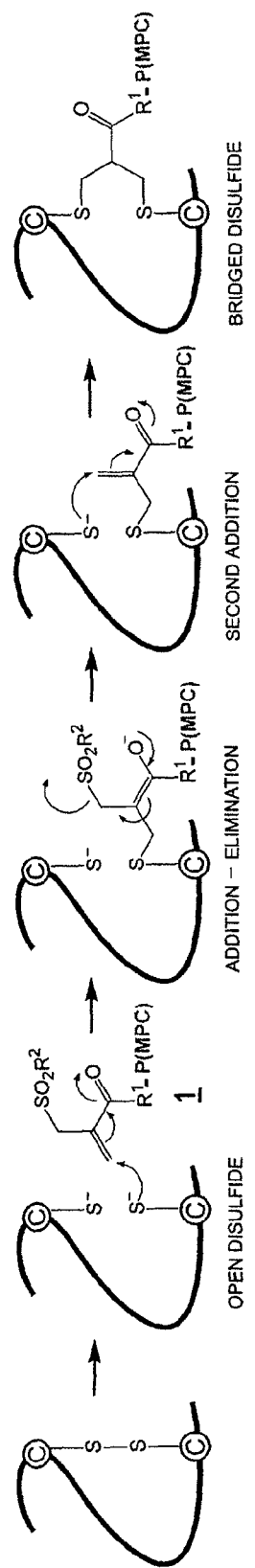
Figure 2:
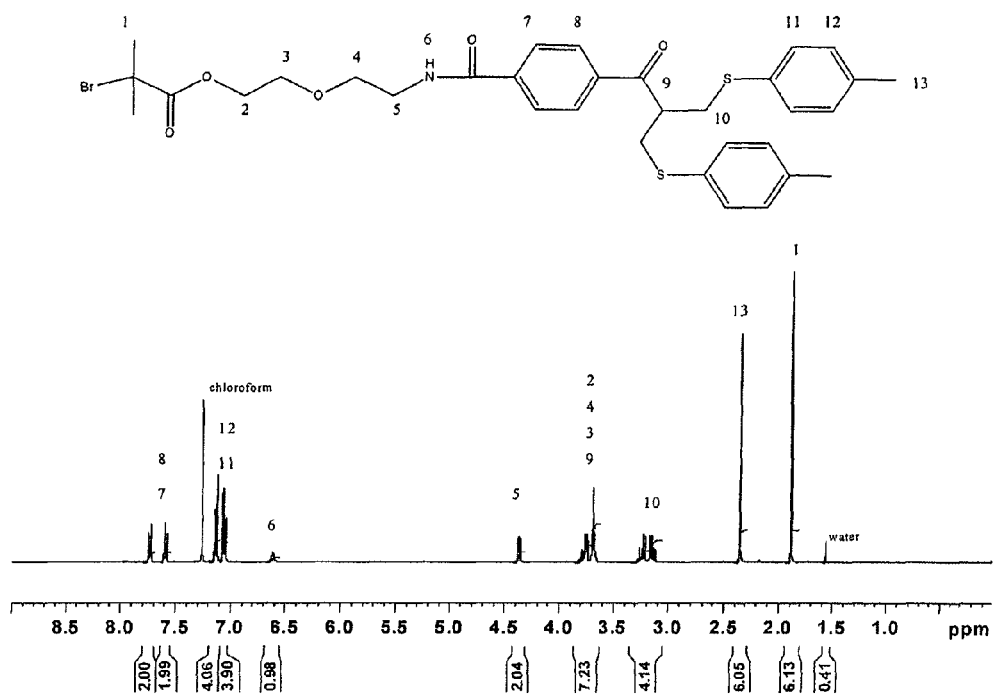
FIG. 2 shows the $^1$H NMR spectrum of initiator (4)

In this invention, such polymers, based upon phosphorylcholine (PC) are functionalised with an end-terminal linking group capable of insertion into the disulfide bridges or reaction with terminal cysteine residues of many commonly used therapeutic proteins. FIG. 1 shows the mechanism of PC polymer insertion.

This invention provides for a method of attaching novel PC polymers, useful for modification of proteins by virtue of their biocompatible properties, much akin to the PEG counterparts. The polymer is moreover, selectively attached at specific positions within the protein structure dictated by the position of the disulfide bridges or terminal cysteine residues in the conformational tertiary structure of the protein.

EXAMPLE 1

Preparation of Benzoic Acid Derivative of the Bis-Sulfide (1)

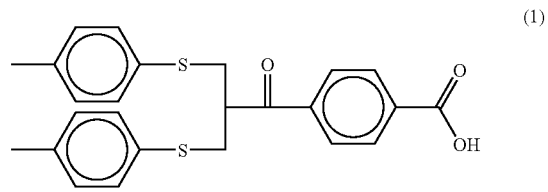

The benzoic acid derivative of the bis-sulfide was prepared as described by Liberatore, F., Eberle, M. & Lawton, R. G. Bioconjug. Chem. 1, 36-50 (1990).

EXAMPLE 2

Preparation of the NHS Ester of the Bis-Sulfide (2)

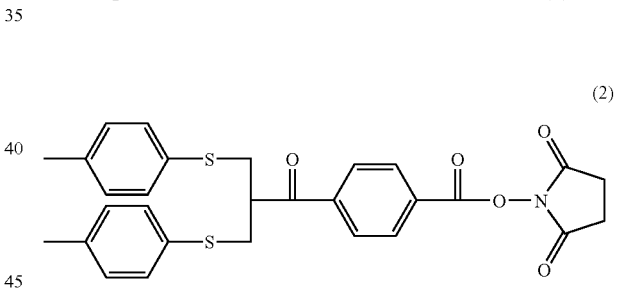

Under an argon atmosphere, a stirred suspension of 4-[2, 2-bis[(p-tolylsulfonyl)-methyl]acetyl]benzoic acid (2 g, 4 mmol), N-hydroxysuccinimide (0,483 g, 4.2 mmol, NHS, Aldrich) and anhydrous dichloromethane (5 ml, Aldrich) was cooled using an ice bath. Neat 1,3-diisopropylcarbodiimide (657 μL, 4.2 mmol, DIPC, Aldrich) was then added dropwise. After 1.5 h, a further 60 μL of DIPC was added, and after 3 h, the reaction mixture was passed through a non-absorbent cotton wool filter. The homogeneous filtrate was diluted with dichloromethane (≈30 ml), washed with water (2×15 ml) and dried with magnesium sulfate. Filtration under gravity and removal of volatiles under vacuum gave the desired active NHS ester as a solid product (1.89 g, 79% yield).

$^1$H NMR: (CDCl$_3$, 400 MHz) δ 2.48 (s, 6H, CH$_3$), 2.94 (s, 4H, CH$_2$CH$_2$), 3.56 (A2B2X, 4H, CH$_2$C), 4.38 (quintet, 1H, CH, J=6.3 MHz), 7.37, 7.70 (AB q, SO$_2$Ar, 8H, J=8.0 & 8.3 MHz resp.), 7.76, 8.14 (AB q, COAr, 4H, J=8.6 MHz). 13C NMR: (CDCl$_3$, 400 MHz) δ 195.29, 168.92, 160.95, 145.63, 139.11, 135.29, 130.92, 130.24, 129.59, 128.73, 128.28, 55.67, 35.89, 25.70, 21.70. MALDI-TOF MS: m/z=620.3070 [M+Na]+.

EXAMPLE 3

Preparation of the Bis-Sulfide ATRP Initiator

Step 1: This step was performed to place a spacing unit into the initiator that would enhance the compounds' solubility in methanol, the solvent selected for the eventual polymerization (scheme 1). A 50 ml round bottom flask was charged with NHS ester bis-sulfide compound (1 g, 1.88 mmol, 1 equivalent) and a magnetic stir bar. The flask was sealed with a septum and purged with argon for approximately 1 min. Under stirring at room temperature, neat 2-(2-aminoethoxy) ethanol (207 µl, 2.13 mmol, 1.13 equivalents) was added dropwise by syringe. The resulting solution was allowed to stir at RT overnight. After stirring for 20 h, the solvent was removed under vacuum to leave a sticky residue which was immediately dissolved in ethyl acetate (50 ml) and this organic phase was washed with 3×30 ml of deionised water (the last 30 ml acidified with several drops of 0.1 N HCl) and with a saturated brine solution (30 ml). The organic phase was then dried with magnesium sulfate, filtered under gravity and the solvent removed under vacuum in a 100 ml round bottom flask. The sticky residue afforded was further dried in a vacuum oven at RT overnight and used without further purification. The mass was not recorded due to the difficulty in weighing the sample but the yield was assumed to 100% for the next step.

added. Anhydrous dichloromethane (10 ml) was added by syringe and a homogenous solution was allowed to form. Under stirring, neat 2-bromoisobutyryl bromide (225 µl, 2.06 mmol, 1.1 equivalents) was added by syringe. Next, 4-dimethylaminopyridine (11 mg, 0.05 equivalents) in dichloromethane (1 ml) was added and the resulting solution allowed to stir at RT overnight. The reaction solution was diluted with ethyl acetate (50 ml) and washed with deionised water (50 ml), 0.1 M sodium bicarbonate (15 ml), deionised water (15 ml) and finally with saturated brine (20 ml). The organic phase was dried with magnesium sulfate, filtered under gravity and volatiles removed under vacuum to leave a sticky product that was allowed to further dry in a vacuum oven at RT. Analysis by $^1$H NMR showed the product to be contaminated with a small amount of NHS ester starting compound from step 1. Therefore, final purification was achieved using dry flash chromatography. A no. 2 sintered glass funnel (4 cm diameter) was filled with approximately 3 cm depth of silica (BDH, code 153325P). A portion of the product (0.3 g) was dissolved in a small volume of dichloromethane and added to the silica. The column was eluted with 25 ml portions of dichloromethane, ethyl acetate:hexane (1:2 v/v), ethyl acetate:hexane (1:1.5 v/v) and ethyl acetate:hexane (1:1 v/v). The elution of compounds was followed by TLC analysis (ethyl acetate:hexane 1:1 v/v, UV lamp detection) of the fractions obtained. The ethyl acetate:hexane

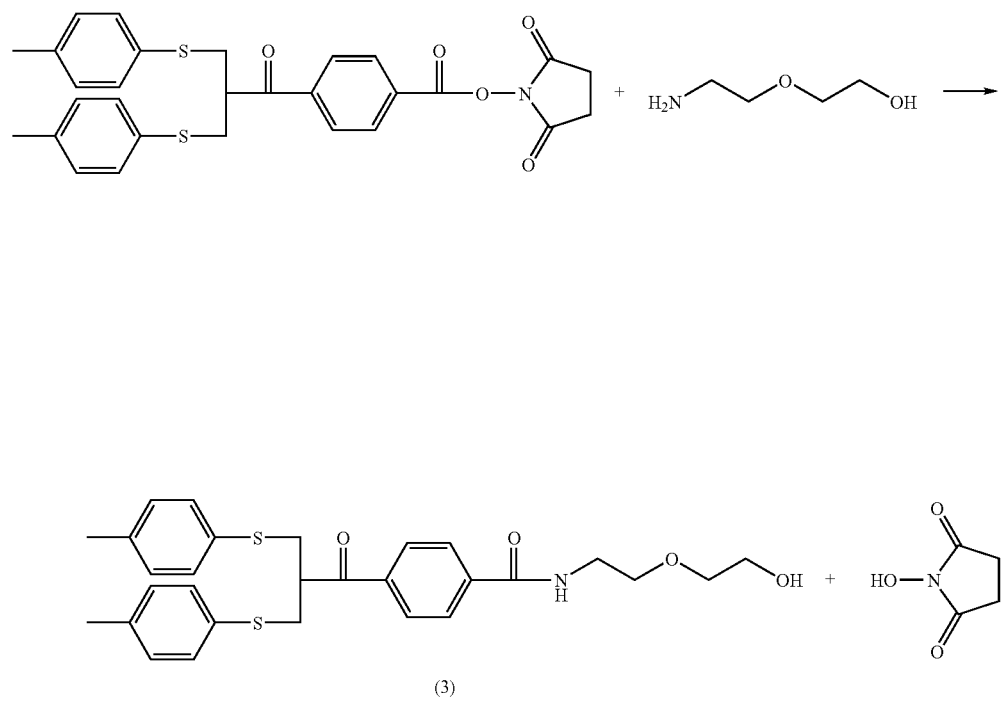

Step 2 (scheme 2): The residue contained in the 100 ml round bottom flask (3) was sealed with a septum and placed under an argon atmosphere. A magnetic stir bar was also (1:1.5 v/v) fractions were shown to contain the major product (Rf about 0.4) and these fractions were combined and volatiles removed under vacuum to leave the final product ((4) 0.13 g).

Scheme 2: Synthesis of ATRP initiator (4)

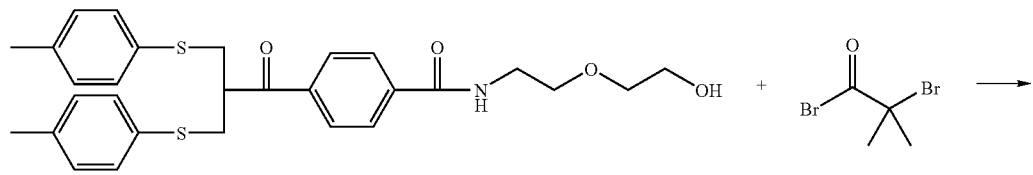

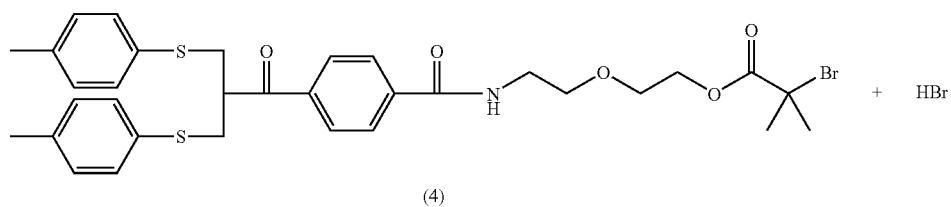

(4)

EXAMPLE 4

MPC Polymer Synthesis Using Bis-Sulfide Linker (4) as ATRP Initiator

A typical ATRP synthesis of MPC homopolymer from bis-sulfide initiator (4) is shown in the Scheme 3. Bis-sulfide initiator (4) (120 mg, 0.18 mmol) was dissolved in 5 mL methanol. After the solution was purged with nitrogen for 40 min, catalysts Cu(I) Br (25.8 mg, 0.18 mmol) and bipyridine (56.2 mg, 0.36 mmol) were added to the reaction flask, followed by the addition of MPC monomer (3.68 g, 12.6 mmol) at 20° C. The reaction was stirred under nitrogen atmosphere overnight, and was stopped by adding excess methanol. The MPC polymer (5) was purified by passing through a silica gel column [silica gel 60 (63-200 mm)] to remove the catalysts, and being further precipitated in acetone solvent. The collected polymer was vacuum dried. Scheme 3 shows the synthesis of MPC homopolymer (5) by ATRP.

Scheme 3: Synthesis of MPC homopolymer (5)

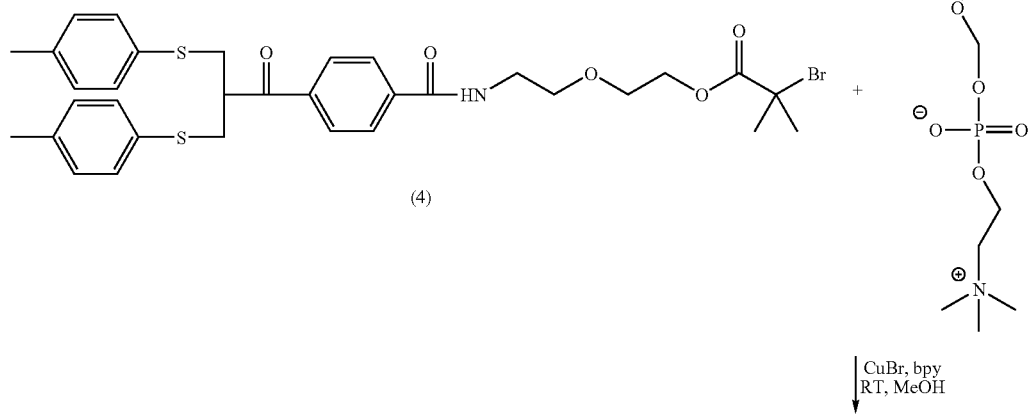

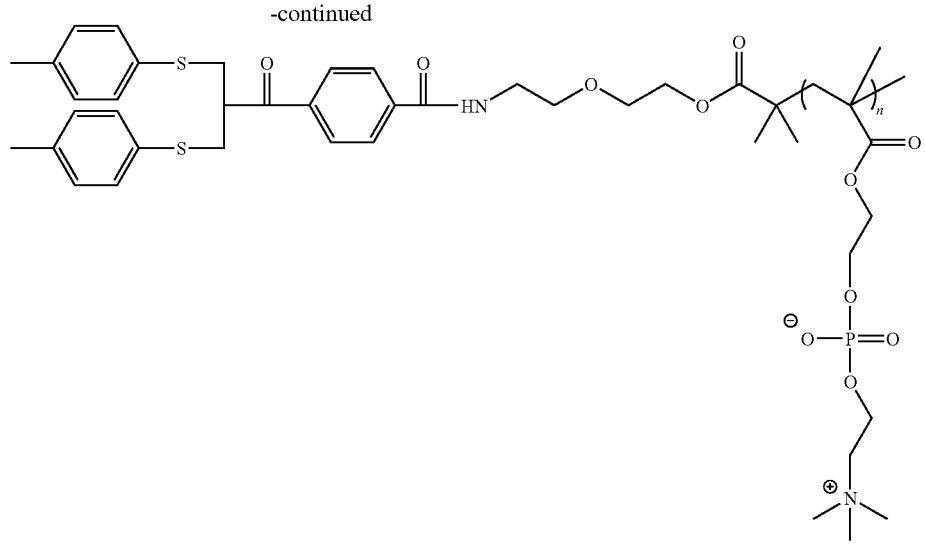

(5)

EXAMPLE 5

Oxidation of the Bis-Sulfide MPC Polymer to Bis-Sulfone (6)

To ensure that efficient protein conjugation could be performed with MPG polymers of type (5) it was necessary to oxidise the bis-sulfide end group to the desired bis-sulfone (Scheme 4). The thiol ether selective oxidation reagent Oxone (Aldrich) was used to achieve this mild oxidation.

Scheme 4: Conversion of Bis-sulfide (5) to Bis-sulfone (6)

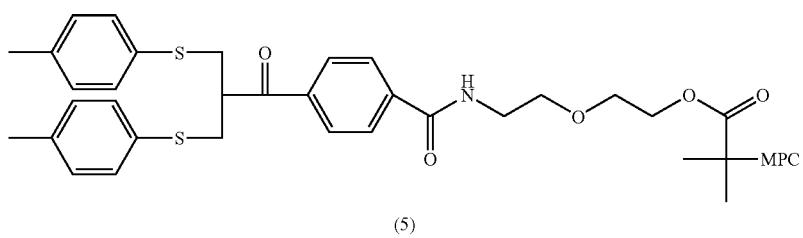

(5)

Oxone
methanol:water 1:1

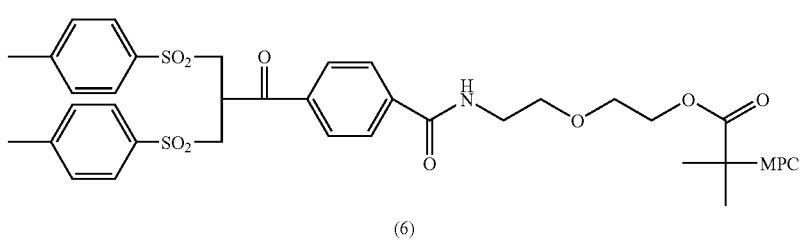

(6)

Figure 3A:
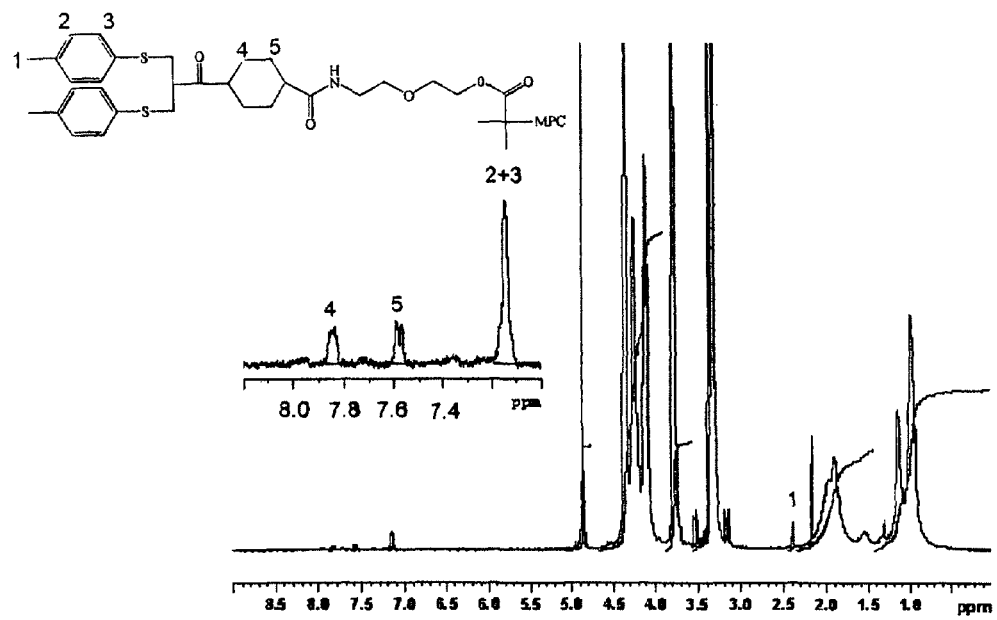
FIGS. 3a and 3b show the $^1$H NMR spectra of MPC polymer with bis-sulfide (5(1)) and bis-sulfone (6(1)) end groups respectively.
Figure 3B:
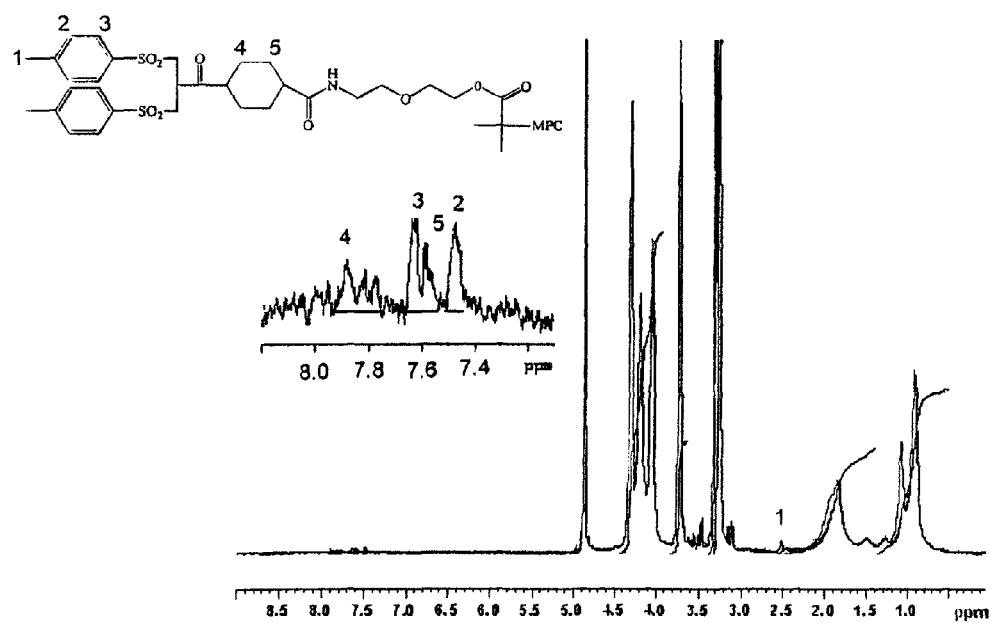

Proton NMR analysis of the product (6) from oxidation was consistent with the desired structure (FIG. 3a). Signals for the aromatic groups of the linker moved further down field (see protons labelled 1, 2, 3, 4 & 5 in FIGS. 3a & 3b) in the $^1$H NMR spectrum compared to the precursor starting polymer (5). As expected, all starting bis-sulfide (5) was oxidised. There was no evidence that any other functional group in the MPC polymer (5) was affected during the oxidation. The PEG equivalent Mw of (5) and the oxidised product (6) were calculated by SEC. The characterisation results of various polymers are listed in Table 1.

TABLE 1

Characterisation data for various MPC polymers

| Polymer No. | | Mn (NMR) | Mn (SEC, RALS detector) | PD |
|---|---|---|---|---|
| 5(1) | Bis-sulfide linker-MPC | 56,000 | 44,900 | 1.28 |
| 6(1) | Bis-sulfone linker-MPC | 35,100 | 41,800 | |
| 6(2) | Bis-sulfone linker-MPC | 62,500 | 37,800 | 1.19 |
| 6(3) | Bis-sulfone linker-MPC | 47,800 | 21,200 | 1.20 |
| 6(4) | Bis-sulfone linker-MPC | 41,300 | 25,500 | 1.24 |

EXAMPLE 6

Conjugation of MPC Bis-Sulfone to IFN

Before the conjugation of MPC bis-sulfone (6(1)) to IFN, the MPC polymer (5(1)) was further fractioned by using Superdex™ 200 protein SEC column. The fraction of elution which was equivalent to PEG 20 k Da was collected and oxidised to bis-sulfone as described in Example 5.

To 1.00 ml of Interferon-α (IFN) (0.3 mg/ml) in PBS (pH 7.85, 2 mM EDTA) was added dithiothreitol (DTT, 15.4 mg, 100 mM, excess) and after vortexing for several seconds until homogenous the resulting solution was allowed to stand at room temperature for 30 mins. The solution was then diluted with fresh buffer (500 μl) to give 1.50 ml in total. The DTT was removed and the buffer changed to PBS pH 8.20, 5 mM EDTA, using a protein desalting column (HiTrap, Amersham Biosciencse, 17-1408-01). The column was eluted with 1 ml followed by 0.8 ml of buffer after the sample was loaded. The two elutes, collected separately ($A_{280\ nm}$=0.068 and 0.093 respectively), were combined and 20 μl taken for further analysis on SDS PAGE. MPC bis-sulfone (4 mg, (6)) was added to the 1.8 ml of reduced protein and after vortexing until homogeneous the solution was kept at 4'C overnight without stirring or agitation. A sample (20 μl) was taken for PAGE analysis and to the remaining solution was added 100 μl of an oxidising glutathione solution (prepared from 1.5 mg reduced glutathione and 3.0 mg oxidised glutathione dissolved in 1 ml of PBS pH 8.2) and stored at 4° C. overnight.

Figure 4:
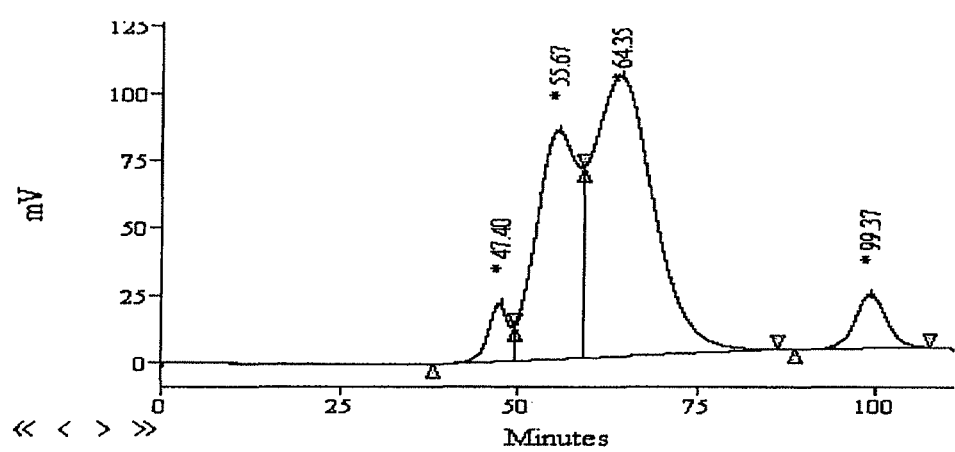
FIG. 4 shows the SEC trace of PCylated IFN after removal of the free polymer.

FIG. 4 shows the SEC trace which confirmed the presence of mono-(64.35 min) and di-PCylated IFN (55.67) plus some aggregate (47.40 min), together with the free IFN (99.37 min).

Figure 5:
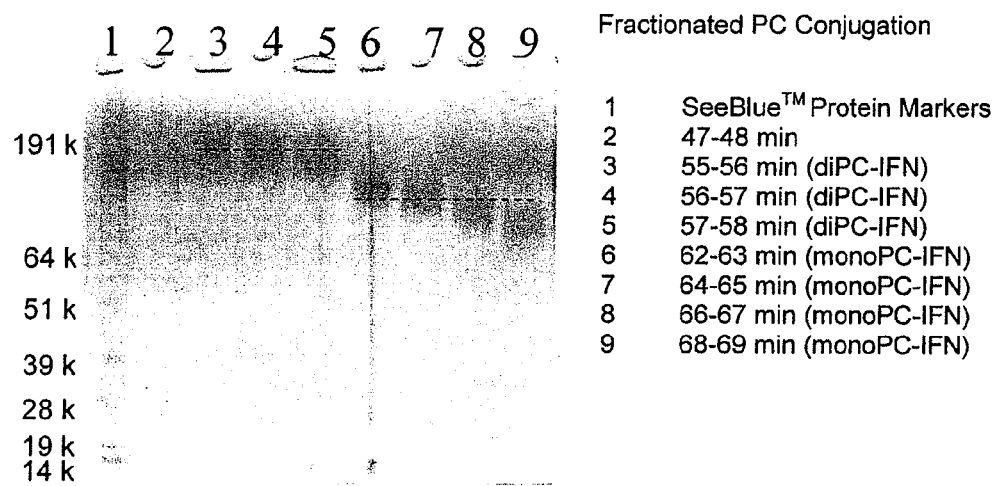
FIG. 5 shows the SDS-PAGE of SEC fractions obtained from fractionated PC conjugation to IFN.

The SEC fractions obtained from the fractionated PC-IFN conjugate were taken and run on an SDS-PAGE (4-12% Bis-Tris gel, MOPS buffer, non-reducing conditions, silver staining). FIG. 5 shows the PAGE trace which clearly shows two distinct sets of bands separated by lanes 5 and 6, one set mid-way between the 64 k and 191 k markers and the other at the 191 k marker boundary, which correspond to the mono and di-PCylated IFN species as seen on the SEC trace in FIG. 4.

EXAMPLE 7

Western Blots of PEG-IFN and PC-IFN Conjugates

Figure 6:
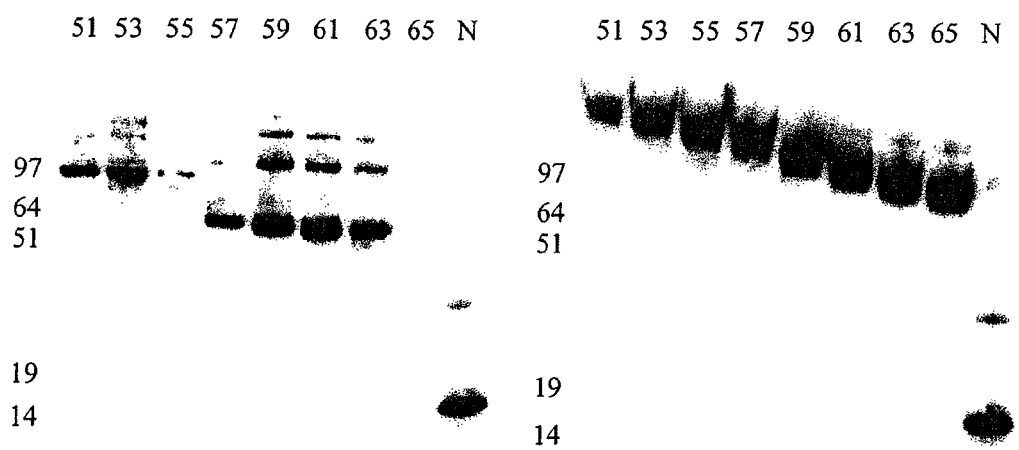
FIG. 6 shows the Western Blot analysis of PEG-IFN (left side gels) and PC-IFN (right side gels) after incubation for 1 week at 4° C., ambient (20° C.) and 37° C.

PCylated IFN and a comparative PEGylated IFN prepared using the same bis-sulphone linker as described in WO2005/007197 were subjected to Western blot analysis using a polyclonal antibody against IFN alpha (FIG. 6). In FIG. 6, numbers on the top relate to the time of elution of the sample from SEC. Native IFN-α is denoted as N. The primary antibodies were incubated for 48 hours. Optimisation of antibody dilution and the length of incubation was required to improve the detection of PC-IFN.

PEGylation is known to cause steric shielding and consequently affects the way an antibody binds to a PEGylated protein. One aim of Western blot analysis was to assess the extent of steric shielding caused by PCylation in comparison to PEGylation. When equal loadings of PEG-IFN and PC-IFN were analysed (as determined by the height of the SEC trace peak at specific time points), no bands were detected for PC-IFN (data not shown).

To facilitate the detection of PC-IFN bands, larger volumes of PC-IFN were required. The largest volume of PC-IFN (20 μl) was therefore loaded as shown in Table 2 and a longer incubation protocol was employed (48 h incubation with 1:10,000 anti-IFN primary antibody). It is to be noted that since the PEG-IFN samples were more dilute than the PC-IFN conjugates, is was not possible to match the highest PC conjugate concentration with the PEG samples due to the restriction in PAGE sample loading volume.

TABLE 2

Height of SEC trace and the gel loading volume for Western blot analysis.

| Time | Height of SEC trace (mV) | | SDS-PAGE loading (μl) | |
|---|---|---|---|---|
| (min) | PEG-IFN | PC-IFN | PEG-IFN | PC-IFN |
| 51 | 19.4 | 25 | 20* | 20 |
| 53 | 55.5 | 61.4 | 20* | 20 |
| 55 | 35.5 | 81.8 | 20* | 20 |
| 57 | 22.6 | 77.3 | 20* | 20 |
| 59 | 100 | 70.5 | 14.1 | 20 |
| 61 | 174 | 77.3 | 8.9 | 20 |
| 63 | 74.2 | 97.7 | 20* | 20 |
| 65 | 16.1 | 102.3 | 20* | 20 |

*Loading limit of the gel used.

As shown in FIG. 6 (wherein left and right gels are PEG-IFN and PC-IFN respectively, and native IFN-α is denoted as N), the resulting Western blot gave intense bands for PC-IFN, confirming the presence of IFN. The migration of the bands obtained correlate with the PAGE gel obtained in FIG. 5. This result strongly suggests that there may be more steric hindrance of the protein to antibody caused by PC compared to PEG polymer.

EXAMPLE 8

Stability of Purified PCylated IFN Conjugates and Comparison with PEG-IFN

Figure 7:
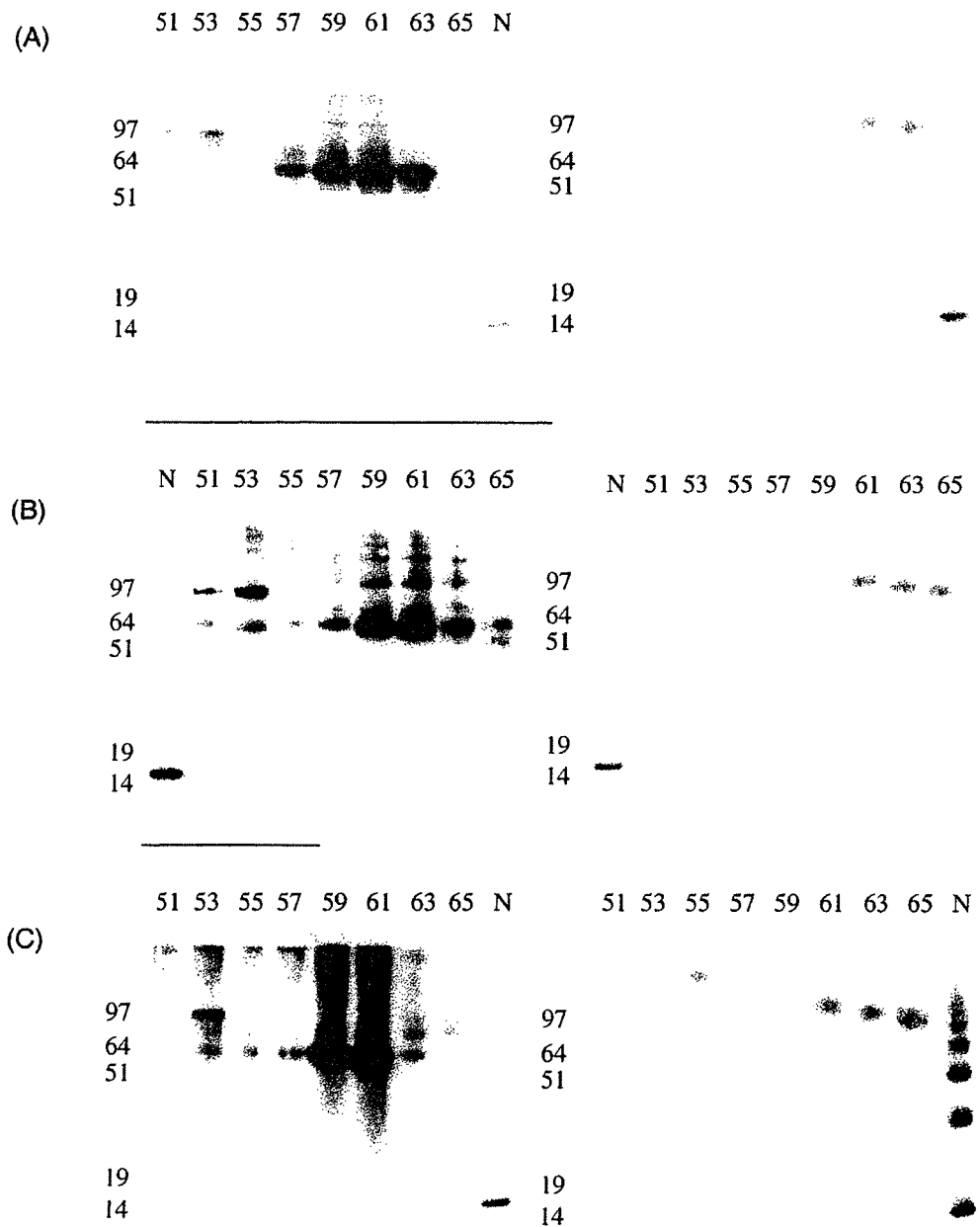
FIG. 7 shows the Western Blot analysis of PC-IFN samples after incubation for 1 week at 4° C. (A), 20° C. (B) and 37° C. (C)

The PC-IFN conjugate samples obtained from the SEC run presented in FIG. 4, were incubated at 4° C., ambient temperature (20° C.) and 37° C. for one week and analysed by Western blot (FIG. 7) to assess stability.

After the 7 day incubation and at all temperatures, both PC and PEG samples showed excellent stability. All samples remained as high MW bands indicating no breakdown and release of IFN from either PC or PEG conjugates.

Unconjugated IFN-α aggregated readily under storage at 37° C. For conjugates, there was a progressive propensity to form aggregates with increasing storage temperature and a difference was seen between PC and PEG samples. With PEG-IFN samples at 4° C., predominantly unaggregated bands were observed. At RT and 37° C., multiple bands of higher MW were clearly visible across all time points, presumably relating to aggregated species. Surprisingly, this effect was less for the PC samples, where the high MW aggregate band was only visible at 37° C. This suggests that the PCylated IFN has a lower tendency to aggregate than PEGylated IFN.

In summary, from Examples 7 & 8 we can conclude that PC-IFN did interact as easily with the primary antibody as well as PEG-IFN, indicating the PC polymer may be causing greater steric hindrance than the PEG polymer. This could result in lower opsonisation in vivo and hence longer residence time. If the steric effects reduced interaction with the target ligands, then there might also be option to administer a higher dose without toxicity.

The PC-IFN had a tendency for far less aggregation than the PEG-IFN, even at 1 week at 37° C. This could provide formulation advantages. It might also mean that the conjugate may not be lost as easily during manufacture and storage by interaction with the separating columns or the glass storage vials.

Furthermore, we found that the PC-IFN conjugate is stable at 1 week at 37° C. with no signs of loss of polymer from the conjugate. The linker is therefore stable and thus no loss of protein from the system should occur in vivo.

EXAMPLE 9

Preparation of Polymers and Conjugates for In Vitro Evaluation Size-Exclusion Chromatography (SEC) for MW Determination The SEC system comprised a guard column and two Viscotek 7.8 mm×30 cm $GMPW_{xl}$ columns connected to a Viscotek Model 270 series dual detector (right-angle laser light scattering (RALLS) and viscometer) and a Viscotek VE 3580 RI detector. The three detectors together comprised the 'TriSEC system' referred to herein. The equipment was calibrated using a PEG standard of MW 21,450 (Polymer Laboratories). The SEC eluent used was either 0.2 M $NaNO_3$ with 10% acetonitrile or PBS at pH 7.3 using a flowrate of 0.7 ml/min. The TriSEC system was controlled using Viscotek OmnicSEC 3.1 software. Samples were prepared at a concentration between 3 and 5 mg/ml in the eluent and filtered through 0.2 μm Anotop 10 filters (Whatman, cat. no. 6809-1022). All samples were run in triplicate and the results averaged. The do/dc value used (0.142) obtained from a standard ATRP MPC polymer as described in WO02/28929 of Mn58,000, Mw 68,900 and Mw/Mn of 1.19, run at concentrations of 5, 4, 3, 2 and 1 mg/ml (from a stock solution of 80 mg 792BB/13 in 4 ml buffer) and using the OmniSEC software. Conventional calibration was obtained using a set of PEG standards (Polymer Laboratories and Fluka) with Mp values of 167.7, 126.5, 82.3, 40.0, 19.2 and 12.3 kDa on the same SEC system.

Fractionation of MPC Polymers

Aqueous solutions (150 mg/ml) of two MPC bis-sulfide polymers, both target degrees of polymerisation (Dp) of 20 made as per Examples 1-4 (2 ml), were separately prepared. For the first, 2×1950 μl was run separately on the SEC system described above (Superdex 200 column) running in pH 4.0, 20 mM sodium acetate at 1 ml/min and with UV detection at 280 nm. Fractions of elute were collected every 1 minute during peak elution and stored at 4° C. until required. The second sample was run once (also 1950 μl injected) under the same conditions.

MPC bis-sulfones, 12, 20 and 30 kDa PEG equivalent MWs, ran on SEC with sodium acetate buffer, pH 4.0, resulted in peaks whose retention times at the maximum peak height were 70.50, 61.25 and 55.38 min respectively. Therefore, all the 69-70, 70-71 and 71-72 min fractions were combined (9 ml); as were the 60-61, 61-62 and 62-63 min fractions (9 ml). The 54 to 56 min fractions were not considered concentrated enough to give enough polymer for conjugation, therefore the 57-58, 58-59 and 59-60 min fractions were combined (9 ml).

Each of the three 9 ml samples were then concentrated to about 1 ml using a Vivaspin 6 ml centrifugal concentrator (MWCO 5 kDa, 4 k rpm) ready for oxidation of the end group to the bis-sulfone which is described below.

Oxidation of Fractionated MPC Bis-Sulfide To MPC Bis-Sulfone

The three concentrated samples from the fractionation step were separately diluted with methanol (1 ml) and Oxone (5 mg) added to each. The resulting mixtures (2 ml) were allowed to stir at RT overnight. The liquid phases were then isolated by centrifugation followed by decantation. Each solution was diluted to 2.5 ml with fresh deionised water and then buffer exchanged/purified using PD-10 columns (Pierce) pre-equilibrated with deionised water. The purification resulted in three 3.5 ml solutions to which was added chilled acetone (10 ml to each). The resulting precipitates were isolated by centrifugation (4 k rpm for 15 min) and allowed to dry under vacuum at RT to give three solid products. These were coded Poly9(1) (46 mg), Poly9(2) (27 mg) and Poly9(3) (18 mg) for 12, 20 and 30 kDa MPC respectively. All samples stored under argon at −18° C. until needed.

After oxidation of the end-group to the bis-sulfone form, two of the MPC polymers that were fractionated with pH 4.0 acetate as the mobile phase gave peaks consistent with their fractionation conditions (20 and 30 kDa PEG equivalent MWs). For the MPC bis-sulfone obtained using from SEC fractions that eluted after 70 min (12 kDa PEG equivalent MW), the chromatogram was broad. One possibility is that the broadness was a consequence of the excellent separation of the Superdex 200 protein column at this molecular weight, since the same sample run on a more traditional SEC column (Triple detection SEC data) gave a low polydispersity (Mw/Mn=1.12) only slightly broader than the higher MW samples (Mw/Mn=1.07 for both 20 kDa & 30 kDa equivalent MPC polymers). Interestingly, after conjugation with IFN, analysis of the resulting product by PAGE and western blot suggested that this may actually be a heterogeneous polymer (see in vitro analysis below).

Conjugation of MPC Bis-Sulfone to IFN

The best conditions currently observed for the conjugation of MPC bis-sulfone to IFN are described. IFN-alpha-2a (1 mg, Peprotech cat. no. 300-02A, lot no. 081CY28) was reconstituted from a powder with deionised water (1 ml) and the absorbance checked at 280 nm. The solution was then added to dithiothreitol (DTT, 10 μl of a 0.4 M stock solution, 4 mM DTT final concentration) and after gentle rotation for several seconds until homogenous the resulting solution was allowed to stand at RT for 30 mins. The DTT was then removed and the buffer changed to PBS pH 8.20, 5 mM EDTA, using a PD-10 desalting column (PD-10, GE Healthcare, cat. no.

52-1308-00). The column was pre-equilibrated with the PBS pH 8.20, 5 mM EDTA and the protein solution added. The column was then eluted with 5×1 ml of fresh buffer added, collecting each 1 ml elution separately. Fractions 3 and 4 were identified to be containing reduced protein by their A280 nm readings (typically A280 nm=0.70 and 0.25 respectively) and combined to give 2 ml.

The solution was then added to a fresh 2 ml microfuge tube containing the MPC bis-sulfone polymer (11 mg) and a solution allowed to form with gentle shaking. The solution was then placed in the fridge (4° C.) overnight. An oxidising glutathione solution (50 µl, prepared from 1.5 mg reduced glutathione and 3.0 mg oxidised glutathione dissolved in 1 ml of PBS, pH 8.2) was added and the solution returned to the fridge overnight. The solution was diluted to 2.5 ml with fresh buffer (500 µl) and then buffer exchanged to 10 mM Tris pH 8.0 (no NaCl) using a PD-10 column as per the supplied instructions (GE Healthcare, 3.5 ml solution resulting). The polymer-conjugate was then isolated by ion-exchange chromatography followed by size-exclusion chromatography as described below.

Figure 8:
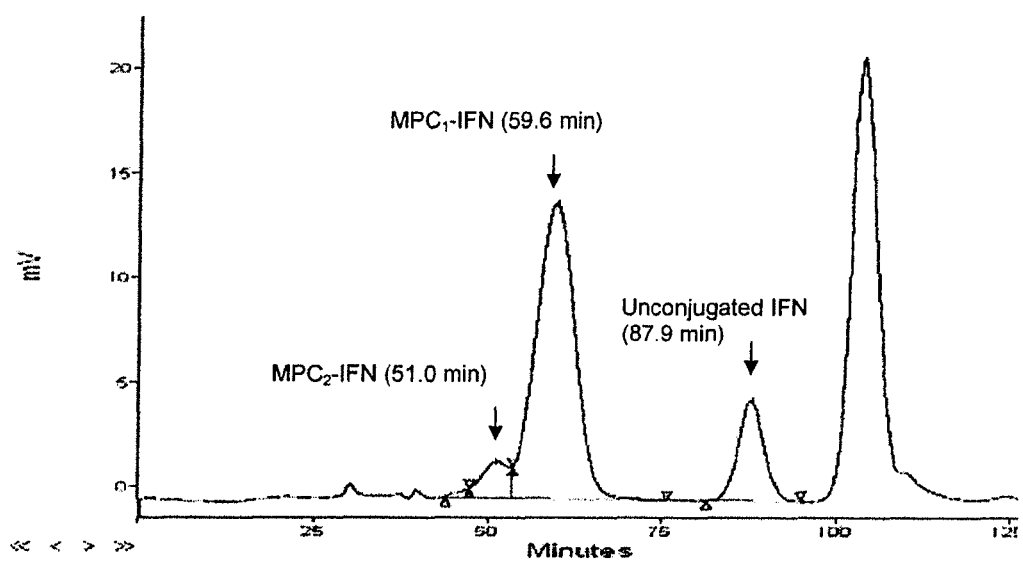
FIG. 8 is an SEC chromatogram showing separation of 20 kDa PEG equivalent MPCylated IFN sample (Con9(2))
Figure 9:
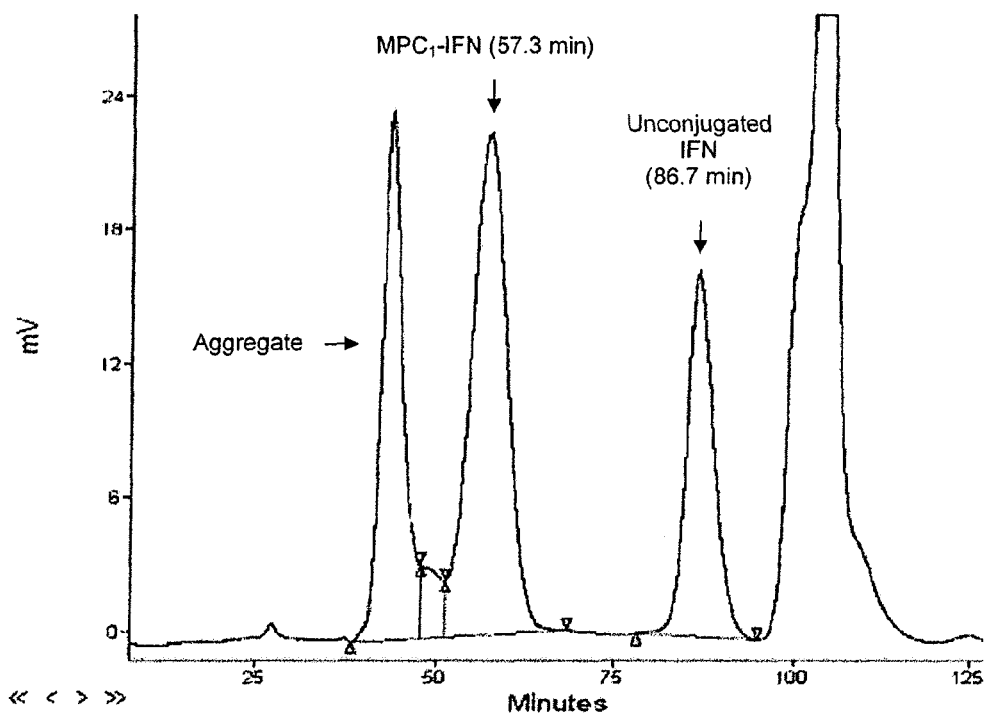
FIG. 9 is an SEC chromatogram showing separation of 30 kDa PEG equivalent MPCylated IFN sample (Con9(3))
Figure 10:
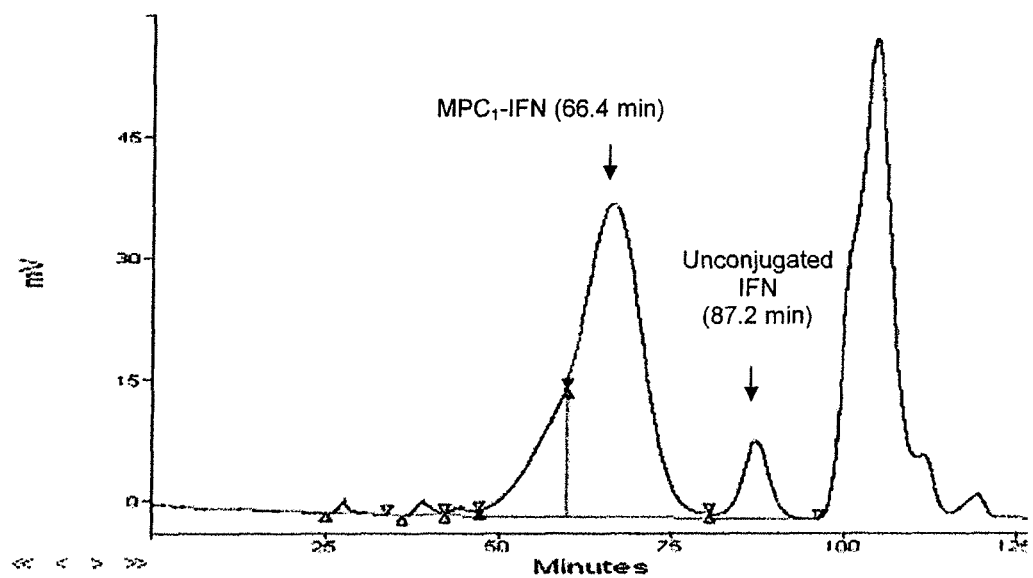
FIG. 10 is an SEC chromatogram showing separation of 12 kDa PEG equivalent MPCylated IFN sample (Con9(1))

Three batches of MPC-IFN were prepared with MPC polymer that was first fractionated to have comparable solution size to 12, 20 and 30 kDa PEG. The SEC chromatograms obtained at the final stage of purification are shown in FIGS. 8-10. In these Figures, the samples are from E2+E3 IEX fractions with a pH 7.3 PMS mobile phase. FIG. 8 shows Con9(2), FIG. 9 shows Con9(3) and FIG. 10 shows Con9(1). A 20 kDa PEG-IFN conjugate was also prepared for comparison. As previous, all batches were purified by IEX followed by SEC. The IEX fractions chosen for SEC were those deemed the most rich in protein species as determined by their $A_{280\ nm}$ readings. Therefore, not all the conjugate possible was isolated, just an amount sufficient for further study. Consequently, the following SEC chromatograms do not necessarily represent the true level of conjugation achieved since the samples had already been semi-purified by IEX chromatography.

Figure 11:
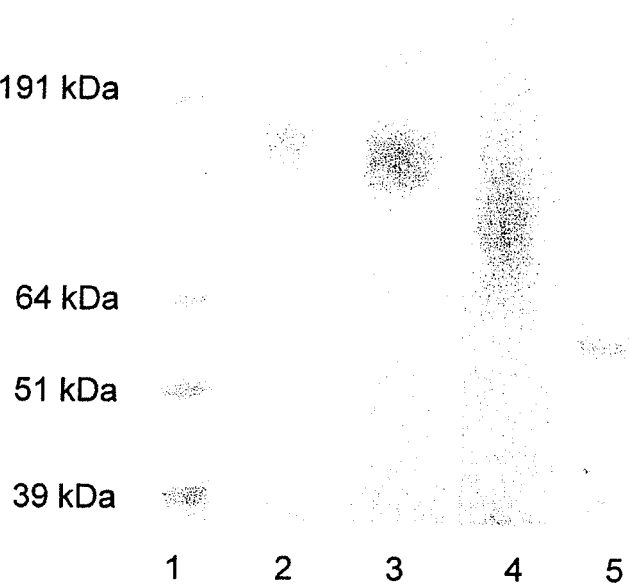
FIG. 11 is an SDS PAGE gel for MPC and PEG interferon conjugates.

All the MPC conjugates had relative MWs of between 65 to 191 kDa by SDS PAGE (FIG. 11). In this SDS run SeeBlue protein markers (Invitrogen) were used on a 4-12% Bis-Tris gel with MOPS buffer under reducing conditions. The 20 kDa PEG-IFN conjugate (Con9(2)) had a relative MW of between 64 and 51 kDa (FIG. 11) and was therefore smaller than all the MPC conjugates by PAGE. It is well documented in the literature that PEG runs 'larger' than an equivalent MW protein in SDS PAGE which separates due to size only. For example, under these conditions, a 20 kDa PEG runs only as far as a protein with an approximate MW of 40 kDa. Consistent with the SEC result, the 12 kDa PEG equivalent MPC sample (Con9(1)) appears to give a higher dispersity conjugate. However it was possible to fractionate the conjugate by using some of the SEC fractions obtained.

Anion Exchange Chromatography and Size-Exclusion Chromatography

A 1 ml HiTrap Q FF column (GE Healthcare, cat. no. 17-5053-01) was equilibrated with 10 mM Tris buffer, pH 8.0 (No NaCl). The protein solution was loaded on to the column using a peristaltic pump and the filtrate collected as the 'load' fraction. The column was then washed with 5×1 ml fractions of fresh 10 mM Tris buffer collecting 5 fractions (W1 to W5) to remove unreacted MPC polymer. The column was then eluted with 5×1 ml fractions of 10 mM Tris buffer containing 0.7 M NaCl to elute all protein species (collecting E1 to E5). Example $A_{280\ nm}$ readings: W5=0.032, E1=0.030, E2=0.748, E3=0.339, E4=0.051, E5=0.028. For all samples, fractions $E^2$ and $E^3$ were identified as containing the highest concentration of protein species by their $A_{280\ nm}$ readings and were subsequently combined and purified by SEC-HPLC in a single run (PBS pH 7.3). Fractions were collected every 1 min during the peak elution and stored immediately at 4° C. For PEG-IFN, $E^2$ was run on SEC without combining with E3. Which SEC fractions were used for in vitro evaluation is described in the in vitro experimental methods below. For identification, the experiment codes were: 12 kDa PEG equivalent MPC-IFN=Con9(1), 20 kDa PEG equivalent MPC-IFN=Con9(2), 30 kDa PEG equivalent MPC-IFN=Con9(3) and 20 kDa PEG-IFN (prepared at pH 7.8, with 1 mg IFN and 1.4 mg PEG bis-sulfone)=Con9(4).

Quantification of Protein in Polymer Conjugates.

The concentration of IFN in the conjugate solutions was determined by BCA assay. The BCA assay was performed as the manufacturer's instructions (Micro BCA assay kit, Pierce, cat. no. 23235). Briefly, 150 µl of reagent was mixed with 150 µl of sample and the absorbance measured at 570 nm. The concentration was determined after obtaining a standard curve from different concentrations of unconjugated IFN standard. The protein content of all SEC fractions were in the range 4-15 µg/ml. The MPC polymer on its own and in the presence of non-conjugated IFN and was shown not to interfere with the BCA assay.

EXAMPLE 10

Antiviral Activity of MPC-IFN Conjugates

The most important in vitro activity of IFN-alpha is its ability to protect cells from virus-induced cytopathic cell death. In this study, we have used human A549 lung fibroblast cells and encephalomyocarditis virus (EMCV), which are reliably and routinely used in IFN-α studies. The samples used for the antiviral in vitro study were obtained directly from SEC using the conjugates described in Example 9: 12 kDa MPC-IFN=Con9(1); 20 kDa MPC-IFN=Con9(2); 30 kDa MPC-IFN=Con9(3) and 20 kDa PEG-IFN=Con9(4).

A549 cells cultured in DMEM supplemented with 10% foetal calf serum (FCS) and antibiotics (penicillin/streptomycin) were trypsinised and suspended at a concentration of $0.2 \times 10^6$ cells/ml. Cells were then plated at 50 ml/well on a 96-well flat-bottom tissue culture (TC) plates and were allowed to adhere at 37° C. On the following day, MPC-IFN samples were diluted in DMEM/10% FCS at twice the desired concentration and added to wells (50 ml/well) in quadruplicates. After 24 h, media was removed and an inoculum of EMCV that causes cell death in positive wells within 24 h was added to each well (50 ml/well). The TC plates were cultured until virus-induced cell death was observed in 80% of wells. Media containing the virus was removed and the cells washed with PBS to remove cellular debris. Cells were then stained with 4% formaldehyde/0.1% methyl violet 2B (50 mg/well) for 30 minutes. Stain was then removed, and the TC plate washed twice with PBS and air dried. Wells stained purple indicates the presence of A549 cells protected from EMCV-induced cell death. Stain was solubilised in 10% SDS (50 ml/well) and the absorbance measured at 570 nm.

Antiviral activity is a well described and widely accepted procedure for the biological evaluation following any modification of IFN. It is the primary measure of in vitro biological activity of IFN and PEGylated IFN. IFN conjugated with 12 kDa, 20 kDa and 30 kDa PEG equivalent molecular weight MPC polymers were tested in this assay and their results compared to native IFN and PEGylated IFN.

The antiviral activity of IFN-alpha-2a (as used in this study) is also reported in the literature and was used as an internal standard to confirm the validity of the antiviral assays that were performed with MPC-IFN. The $ED_{50}$ of IFN was evaluated to be 12±1 pg/ml (n=4). Representative antiviral assay graphs for the polymer conjugates are presented in FIG. 12 and the averaged values presented in Table 3.

TABLE 3

Antiviral assay $ED_{50}$ values for MPCylated and PEGylated IFN conjugates.

| Sample | PEG Equivalent molecular weight | $ED_{50}$ (pg/ml) | % of IFN activity |
| --- | --- | --- | --- |
| IFN | — | 12 ± 1 | 100% |
| PEG-IFN (Con9(4)) | 20 kDa | 75 ± 30 | 16.1% |
| MPC-IFN (Con9(2)) | 20 kDa | 66 ± 10 | 18.1% |
| MPC-IFN (Con9(3)) | 30 kDa | 255 ± 41 | 4.7% |
| MPC-IFN (Con9(1)) | 12 kDa | >4,600 | 0.3% |

Values are averaged from multiple repeats (see experimental section). Experiments from these $ED_{50}$ values were selected from have been verified using IFN as control.

Consistent with expectations for PEGylated proteins, the 20 kDa PEG-IFN had a higher $ED_{50}$ value (i.e, less activity) than unconjugated IFN, which was measured to be 75±30 pg/ml (n=3). Like PEG-IFN, all the MPCylated IFN samples had antiviral activity. The 20 kDa PEG equivalent MW MPCylated IFN sample gave an $ED_{50}$ value (66±10 pg/ml, n=6) and is comparable to the 20 kDa PEG-IFN. This indicates that MPC and PEG of the same hydrodynamic volume affects the antiviral activity similarly in vitro.

The 30 kDa PEG equivalent MW MPCylated IFN gave a lower $ED_{50}$ value than for the 20 kDa samples at 255±41 pg/ml (n=4). This is the general trend that is observed in the literature and could be due to the larger size of the MPC polymer causing greater steric shielding compared to the 20 kDa samples. Since MPC is zwitterionic there may be other features of MPC that influence activity that are not present with PEG. There is still significant activity with the MPC 30 kDa (PEG equivalent) conjugate. Both the 20 and 30 kDa PEG equivalent MPC-IFN conjugates display in vitro activity that warrants evaluation of pharmacokinetic properties.

Without any information about the pharmacokinetic properties of MPC alone, it is difficult to predict how MPC-IFN will differ from PEG-IFN. It is however quite remarkable that the 20 kDa equivalent MPC-IFN displays in vitro activity that is comparable to the 20 kDa PEG-IFN sample. In contrast, the 12 kDa PEG equivalent MW IFN sample displayed less activity. FIG. 13 shows a Western blot with anti-IFN antibody from PAGE analysis. The 12 kDa Con9(2) and 30 kDa Con9(3) are each PEG equivalent MWs. The PEG sample had 1 day incubation with primary antibody and the MPC samples 3 days. The $ED_{50}$ value was >4,600 pg/ml (n=4). Western blot data for the IFN conjugates (FIG. 13) reveals that the 12 kDa MPC sample may not be as homogeneous as the other samples and may therefore not be a true reflection of 12 kDa MPC-IFN conjugate activity. It is not clear what has happened to the 12 kDa sample but the western blot is heterogeneous (FIG. 13, lane B). It is possible that the sample has aggregated since distinct bands can be seen. The proportion of MPC to IFN may be such as to offer little protection to protein aggregation.

As described in Example 8, PEG-IFN is much better visualised by Western blot compared to the MPC-IFN samples at similar concentrations in this antibody based experiment. Only a single day incubation with primary antibody is required for PEGylated IFN as opposed to three days for MPC samples. This indicates better shielding of the protein by MPC polymer over PEG. It is again interesting therefore that the antiviral results were similar for the 20 kDa MPC and PEG conjugates. Mechanisms of IFN clearance from the bloodstream include not only kidney ultrafiltration, but also digestion by proteases, diffusion into tissues and receptor-mediated cellular uptake. Consequently, the half-life of MPCylated IFN may possibly be extended compared to a PEGylated IFN of the same hydrodynamic volume while retaining equivalent antiviral activity.

EXAMPLE 11

Antiproliferation Assay of MPC-IFN Conjugates

IFN-alpha also has an antiproliferation activity in Daudi cells in vitro. Proliferative activity of Daudi cells were measured by the colorimetric conversion from soluble MTT to insoluble MTT formazan. The samples used for the antiproliferation in vitro study were obtained directly from SEC using the conjugates described in Example 9: 12 kDa MPC-IFN=Con9(1); 20 kDa MPC-IFN=Con9(2); 30 kDa MPC-IFN=Con9(3) and 20 kDa PEG-IFN=Con9(4). Molecular weights for Con9(1), Con9(2) and Con9(3) are all PEG-equivalent MWs.

Daudi cells cultured in RPMI 1640 supplemented with 10% FCS and antibiotics were suspended in $0.2 \times 10^6$ cells/ml and plated into a round-bottom TC plate at 10,000 cells/well (50 ml/well). MPC-IFN samples were diluted in RPMI 1640/10% FCS at twice the desired concentration and 50 ml added to wells in quadruplicates. After 72 h, 20 ml of MIT (Sigma-Aldrich cat. no. M5655-1G; 5 mg/ml in RPMI 1640) was added to each well and incubated for 5 h at 37° C. TC plate was then centrifuged at 1,800 rpm for 10 minutes and the supernatant carefully removed. To each well was added 50 ml of DMSO (Sigma-Aldrich cat. no. 154938-2L), agitated at 600 rpm until MTT formazan crystals were completely dissolved and the optical density measured at 570 nm.

One of IFN's immunomodulatory functions is to decrease the proliferative ability of several types of non-immune cells. Antiproliferative activity of MPCylated and PEGylated IFN was therefore investigated using a well established Daudi cell method (FIG. 14 and Table 4). Compared to unconjugated IFN the antiproliferation activity of the 20 kDa PEG-IFN was 3.9%. The 20 kDa and 30 kDa MPCylated IFN samples both exhibited similar antiproliferation activities to the 20 kDa PEG-IFN with values of 3.2% and 1.1% respectively. These results suggest that the factors which reduce the antiviral activity, such as the steric shielding caused by the presence of PEG or MPC polymer, are similarly influential to the reduction in the protein's antiproliferation activity. Also, as previously seen, the 30 kDa MPCylated IFN was less active than the 20 kDa MPC-IFN. Again, it is not clear whether such a small difference might be a significant factor for in vivo studies. The influence of MPC in vivo due to the zwitterionic charge, greater MPC solution density and the overall steric shielding cannot yet be inferred. The literature value for 40 kDa amine PEGylated IFN-alpha-2b is 2% when compared to unmodified IFN-alpha-2b (Ramon et al. (2005) PEGylated Interferon-alpha2b: A Branched 40K Polyethylene Glycol Derivative, Pharmaceutical Research, 22:1374-1386).

TABLE 4

ED$_{50}$ values for the antiproliferation activities
(Daudi cell assay) of IFN, PEG-IFN and MPC-IFN.

| Sample | PEG Equivalent molecular weight | ED$_{50}$ (pg/ml) | % of IFN activity |
|---|---|---|---|
| IFN | — | 17 ± 2 | 100% |
| PEG-IFN (Con9(4)) | 20 kDa | 435 ± 116 | 3.9% |
| MPC-IFN (Con9(2)) | 20 kDa | 524 ± 113 | 3.2% |
| MPC-IFN (Con9(3)) | 30 kDa | 1,498 ± 330 | 1.1% |
| MPC-IFN (Con9(1)) | 12 kDa | >4,600 | >0.3% |

EXAMPLE 12

Pharmacokinetic Study of MPC-IFN in Mice

Briefly, the time courses were determined according to the predicted half lives of known IFN species (see Table 5). For each time point, 5 mice were injected subcutaneously and at a later time sacrificed and exsanguinated for serum preparation. Serum samples were frozen at −20° C. in 20 μl aliquots and stored in a −80° C. freezer until use.

TABLE 5

Sample collection time points following subcutaneous injection into mice.

| Time (h) after injection | 0.5 | 1 | 2 | 4 | 6 | 12 | 24 | 48 | 72 |
|---|---|---|---|---|---|---|---|---|---|
| IFN-α2a (Roferon-A) | X | X | X | X | X | X | | | |
| 40 kDa PEG-IFN (Pegasys) | | X | X | | X | X | X | X | X |
| 20 kDa eq MPC-IFN | | X | X | | X | X | X | X | X |

Antiviral assay was used to determine the presence of the IFN species. For each time point, one vial from each mouse was pooled. Two sets of pooled serum samples were used for pharmacokinetic analysis. IFN-α2a (Roferon-A, Roche) and 40 kDa PEG-IFN (Pegasys, Roche) were also tested in parallel as reference. Since MPCylated and PEGylated IFN in serum cannot reliably be measured directly, a fixed amount of serum was assayed for each time point and the change in the antiviral activities was used as a measure of the amount of IFN present in the serum, ie. a downward trend in antiviral activity is indicative of IFN clearance. Data analyses were performed using GraphPad Prism software. All statistical values shown are expressed as mean±SEM.

The representative absorption and elimination half-lives of IFN, 20 kDa PEG equivalent MPC-IFN and 40 kDa PEG-IFN (Pegasys) are shown in FIG. 15, and the average values are provided in Table 6. Absorption half-life (▲; t$_{1/2}$abs) and elimination half-life (▼; t$_{1/2}$elim) were measured. Each time point is pooled from 5 serum samples. Roferon-A was used as reference for IFN-α2a (FIG. 15A). IFN showed a mean elimination half-life of 0.8 h (n=3). An accurate absorption half-life could not be measured as no ascending trend was seen with all of the time points despite the doses were given subcutaneously, which suggests that IFN is able to enter the bloodstream within 30 min of subcutaneous injection. The 40 kDa (2×20 kDa branched) PEG-IFN (Pegasys) was used as a second reference (FIG. 15C). In mice, 40 kDa PEG-IFN showed a mean absorption half-life following a subcutaneous injection of 7.4 h (n=3). Elimination half-life was measured as >50 h (n=3) as two out of three values exceeded the range of time course (>60 h). This is consistent with the literature.

The pharmacokinetic result for 20 kDa PEG equivalent MPC-IFN showed a substantial extension of blood retention time over that of unconjugated IFN (FIG. 15B). The absorption half-life of MPC-IFN was determined to be 7.3±0.3 h (n=3). This was comparable to that of 40 kDa PEG-IFN (7.4±0.2 h). The elimination halflife was 24±2 h (n=3). This compares favourably to both IFN (<1 h) and the 20 kDa disulfide bond PEGylated IFN (12.3 h).

TABLE 6

Comparison of absorption and elimination half-lives
of IFN (Roferon-A), 20 kDa PEG equivalent MPC-IFN
and 40 kDa PEG-IFN (Pegasys).

| | Absorption t$_{1/2}$ | Elimination t$_{1/2}$ | t$_{max}$ |
|---|---|---|---|
| IFN (n = 3) | <0.5* | 0.8 ± 0.1 | 0.8 ± 0.2 |
| 20 kDa Peg eq MPC-IFN (n = 3) | 7.3 ± 0.3 | 24 ± 2 | 16 ± 4 |
| 40 kDa PEG-IFN (n = 3) | 7.4 ± 0.2 | >50** | 16 ± 4 |
| 20 kDa PEG-IFN [1] | 3.3 | 12.3 | 4 |

[1] Shaunak S, et al. Site-specific PEGylation of native disulfide bonds in therapeutic proteins. Nature Chem. Bio. 2, 2006, 312-313.

*No data point before 0.5 h;

**two t$_{1/2}$ values > 60 h

Alternatively, data points from individual data sets were pooled (n=8) to obtain a combined pharmacokinetic profile for the native, MPCylated and PEGylated IFN. Data points were expressed as a percentage of maximum activity. FIG. 16 and Table 7 illustrates the results obtained from the combined pharmacokinetic profiles. Absorption half-life (▲; t$_{1/2}$bs) and elimination half-life (▼; t$_{1/2}$elim) were measured. Each data point is pooled from 8 experimental sets, expressed as percentage of its maximum activity. Native IFN (Roferon-A) showed an elimination half-life of 1 h (FIG. 16A) while 40 kDa PEG-IFN (Pegasys) had an elimination half-life of >60 h (FIG. 16C). For 20 kDa PEG equivalent MPC-IFN, the elimination half-life was 28.3 h. As previously shown, the absorption half-lives of 20 kDa PEG equivalent MPCIFN and 40 kDa PEG-IFN were very similar. Overall, these results fell within the parameters of pharmacokinetic profiles mentioned in Table 7.

TABLE 7

Combined pharmacokinetic profiles: Comparison of absorption
and elimination half-lives of IFN (Roferon-A), 20 kDa PEG
equivalent MPC-IFN and 40 kDa PEG-IFN (Pegasys).

| | Absorption t$_{1/2}$ | Elimination t$_{1/2}$ | t$_{max}$ |
|---|---|---|---|
| IFN (n = 3) | <0.5 | 1 | 1 |
| 20 kDa Peg eq MPC-IFN (n = 3) | 7.5 | 28.3 | 12 |
| 40 kDa PEG-IFN (n = 3) | 7.4 | >60 | 12 |
| 20 kDa PEG-IFN [1] | 3.3 | 12.3 | 4 |

Taken together, these results clearly indicate that the conjugation of MPC to IFN leads to a substantial extension in the elimination half-life of IFN. Surprisingly, the extension of IFN half-life observed for the 20 kDa PEG equivalent MPC-IFN was greater than the half-life for 20 kDa disulfide bond PEGylated IFN, which is about 12 h. The MPCylated IFN also retains around twice the biological activity of its PEGylated equivalent. Furthermore, MPC polymer provides improved protein shielding from antibodies PEG (as suggested from the Western blotting analysis).

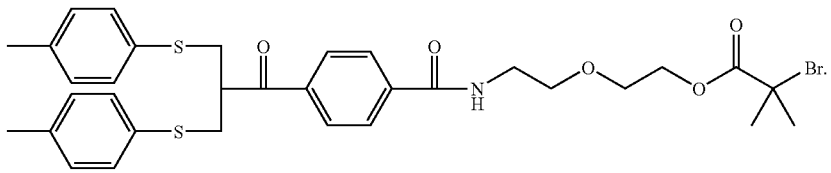 [SMILES: Cc1ccc(SCC(CSc2ccc(C)cc2)C(=O)c2ccc(C(=O)NCCOCCOC(=O)C(C)(C)Br)cc2)cc1]

The invention claimed is:

1. A compound of general formula I

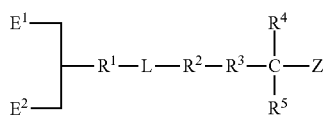

wherein $R^1$ is an electron-withdrawing group and is selected from a keto group, an ester group, and a sulphone group;

$R^2$ is selected from C=O, C(=O)$NR^9$ or a bond; wherein $R^9$ is H or $C_{1-4}$ alkyl;

$R^3$ is selected from the group consisting of $C_1$-$C_{20}$ alkylene, $C_3$-$C_8$ cycloalkylene, C(=O)$R^{10}$, C(=O)$NR^{11}$, $C_1$-$C_{20}$ alkoxy, $C_2$-$C_{20}$ alkenylene, $C_2$-$C_{20}$ alkenyl oxiranylene, arylene, heterocyclene and aralkylene; in which 0 to all of the hydrogen atoms are replaced with halogen, $C_1$-$C_6$ alkyl optionally substituted with 1 to 2 substituents selected from the group consisting of $C_1$-$C_4$ alkoxy, aryl, heterocyclyl, C(=O)$R^{13}$, C(=O)$NR^{11}R^{12}$, oxiranyl and glycidyl;

$R^{10}$ is alkylene of from 1 to 20 carbon atoms, alkoxy from 1 to 20 carbon atoms, oligo(alkoxy) in which each alkoxy group has from 1 to 3 carbon atoms, aryloxy or heterocyclyloxy; any of which groups may have substituents selected from optionally substituted alkoxy, oligoalkoxy, amino (including mono- and di-alkyl amino and trialkyl ammonium, which alkyl groups, in turn, may have substituents selected from acyl, alkoxycarbonyl, alkenoxycarbonyl, aryl and hydroxy) and hydroxyl groups;

$R^{11}$ and $R^{12}$ are independently H or alkyl of from 1 to 20 carbon atoms, or $R^{11}$ and $R^{12}$ may be joined together to form an alkanediyl group of from 2 to 5 carbon atoms, thus forming a 3- to 6-membered ring;

$R^4$ and $R^5$ are each independently selected from H, Z, halogen, $C_{1-20}$ alkyl, $C_3$-$C_8$ cycloalkyl, OH, CN, $C_2$-$C_{20}$ alkenyl, $C_2$-$C_{20}$ alkenyl oxiranyl, C(=O)$R^{13}$, glycidyl, aryl, heterocyclyl, arylkyl, aralkenyl, in which 0 to all of the hydrogen atoms are replaced with halogen, $C_1$-$C_6$ alkyl optionally substituted with 1 to 2 substituents selected from the group consisting of $C_1$-$C_4$ alkoxy, aryl, heterocyclyl, C(=O)$R^{13}$, C(=O)$NR^{11}R^{12}$, oxiranyl and glycidyl, and at least one of groups $R^4$ and $R^5$ is methyl;

where $R^{13}$ is alkyl of from 1 to 20 carbon atoms, alkoxy of from 1 to 20 carbon atoms, oligo(alkoxy) in which each alkoxy group has 1 to 3 carbon atoms, aryloxy or heterocyclyloxy any of which groups may have substituents selected from optionally substituted alkoxy, oligoalkoxy, amino (including mono- and di-alkyl amino and trialkyl ammonium, which alkyl groups, in turn may have substituents selected from acyl, alkoxycarbonyl, alkenoxycarbonyl, aryl and hydroxy) and hydroxyl groups; and L is a linking group wherein the linking group, L, is selected from a bond, a $C_{1-10}$ alkylene group, or an optionally substituted aryl or heteroaryl, any of which groups may have substituents selected from optionally substituted alkoxy, oligoalkoxy, amino (including mono- and di-alkyl amino and trialkyl ammonium, which alkyl groups, in turn, may have substituents selected from acyl, alkoxycarbonyl, alkenoxycarbonyl, aryl and hydroxy) and hydroxyl groups;

Z is selected from the group consisting of Cl, Br, I, $OR^{14}$, $SR^{15}$, $SeR^{15}$, op(=O)$R^{15}$, OP(=O)(=O$R^{15}$)$_2$, O—N($R^{15}$)$_2$ and S—C(=S)N($R^{15}$)$_2$, where $R^{14}$ is alkyl of from 1 to 20 carbon atoms in which each of the hydrogen atoms may be independently replaced by halide, $R^{15}$ is aryl or a straight or branched $C_1$-$C_{20}$ alkyl group, and where an N($R^{15}$)$_2$ group is present, the two $R^{15}$ groups may be joined to form a 5- or 6-membered heterocyclic ring; and $E^1$ and $E^2$ are each, independently, an optionally substituted aryl sulfide group.

2. A compound according to claim 1 in which $R^4$ and $R^5$ are each methyl and $R^3$ is —CO—$R^{10}$ in which $R^{10}$ is oligoalkoxy.

3. A compound according to claim 2 in which $R^{10}$ is an oligoethoxy in which there are 2 to 10 ethoxy groups.

4. A compound according to claim 1, wherein groups $E^1$ and $E^2$ are identical and are a group of formula

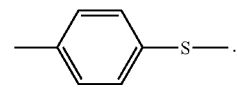

5. A compound according to claim 1 of formula